(12) United States Patent
Kawashima

(10) Patent No.: US 11,786,211 B2
(45) Date of Patent: Oct. 17, 2023

(54) ULTRASOUND IMAGING APPARATUS, METHOD OF OPERATING ULTRASOUND IMAGING APPARATUS, COMPUTER-READABLE RECORDING MEDIUM, AND ULTRASOUND IMAGING SYSTEM

(71) Applicant: OLYMPUS CORPORATION, Tokyo (JP)

(72) Inventor: Tomonao Kawashima, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 338 days.

(21) Appl. No.: 17/171,377

(22) Filed: Feb. 9, 2021

(65) Prior Publication Data
US 2021/0161505 A1 Jun. 3, 2021

Related U.S. Application Data

(63) Continuation of application No. PCT/JP2019/034478, filed on Sep. 2, 2019.

(30) Foreign Application Priority Data

Sep. 14, 2018 (JP) .................................. 2018-172998

(51) Int. Cl.
*A61B 8/08* (2006.01)
*A61B 8/00* (2006.01)
(Continued)

(52) U.S. Cl.
CPC .............. *A61B 8/085* (2013.01); *A61B 8/463* (2013.01); *G01S 15/8977* (2013.01); *A61B 8/0891* (2013.01); *A61B 2018/00595* (2013.01)

(58) Field of Classification Search
None
See application file for complete search history.

(56) References Cited

U.S. PATENT DOCUMENTS

| 2007/0167774 A1 | 7/2007 | Jeong et al. |
| 2009/0069677 A1 | 3/2009 | Chen et al. |

(Continued)

FOREIGN PATENT DOCUMENTS

| JP | 2007-181698 A | 7/2007 |
| JP | 2010-538740 A | 12/2010 |

(Continued)

OTHER PUBLICATIONS

International Search Report dated Nov. 26, 2019 issued in PCT/JP2019/034478.

*Primary Examiner* — Jonathan Cwern
(74) *Attorney, Agent, or Firm* — Scully, Scott, Murphy & Presser, P.C.

(57) ABSTRACT

An ultrasound imaging apparatus includes a processor including hardware. The processor is configured to: generating first frequency spectrum data and second frequency spectrum data with regard to a first ultrasound signal and a second ultrasound signal, respectively; generating first ultrasound image data based on the first ultrasound signal; generating second ultrasound image data based on the second ultrasound signal; estimating a displacement amount including at least one of a positional change amount and a rotation angle of a subject depicted in the first ultrasound image data with respect to the subject depicted in the second ultrasound image data; correcting the first frequency spectrum data in accordance with the estimated displacement amount; calculating differential feature data by using the corrected first frequency spectrum data and the second frequency spectrum data; and generating analysis image data (Continued)

to which color information corresponding to the differential feature data is applied.

14 Claims, 12 Drawing Sheets

(51) Int. Cl.
   *G01S 15/89* (2006.01)
   *A61B 18/00* (2006.01)

(56) References Cited

U.S. PATENT DOCUMENTS

| 2013/0096429 | A1  | 4/2013 | Noguchi |
| 2016/0074015 | A1* | 3/2016 | Eda ................. A61B 8/5269 |
|              |     |        | 600/443 |
| 2018/0035978 | A1  | 2/2018 | Nakatsuji |

FOREIGN PATENT DOCUMENTS

| JP | 2013-128731 A | 7/2013 |
| JP | 2014-233305 A | 12/2014 |
| WO | WO 2009/035627 A2 | 3/2009 |
| WO | WO 2012/063930 A1 | 5/2012 |
| WO | WO 2017/069068 A1 | 4/2017 |

* cited by examiner

ULTRASOUND IMAGING APPARATUS, METHOD OF OPERATING ULTRASOUND IMAGING APPARATUS, COMPUTER-READABLE RECORDING MEDIUM, AND ULTRASOUND IMAGING SYSTEM

CROSS-REFERENCE TO RELATED APPLICATIONS

This application is a continuation of PCT international application No. PCT/JP2019/034478 filed on Sep. 2, 2019, which designates the United States, incorporated herein by reference, and which claims the benefit of priority from Japanese Patent Application No. 2018-172998, filed on Sep. 14, 2018, incorporated herein by reference.

BACKGROUND

1. Technical Field

The present disclosure relates to an ultrasound imaging apparatus that observes a tissue of a patient, an animal, or the like, as a subject by using ultrasound waves, a method of operating the ultrasound imaging apparatus, a computer-readable recording medium, and an ultrasound imaging system.

2. Related Art

As an imaging technique for a subject, such as a living tissue, using ultrasound waves, there is a known technique in which an ultrasound echo backscattered by the subject is received by an ultrasound transducer and is converted into an ultrasound signal and an image is generated based on the ultrasound signal having undergone the conversion. Here, sound wave scattering is a physical phenomenon in which a sound wave and a particle collide with each other in a medium and mutually exert a force (this is called mutual effect) so that the traveling direction of the sound wave is changed. Furthermore, backscattering refers to a component included in the scattering and returning in the direction toward the sound source. Although this phenomenon is also generally called reflection, the term "backscattering" is used below in this application. The sound source here is an ultrasound transducer. An operator, such as a doctor, views the ultrasound image displayed on a display device and based on an ultrasound signal to observe or diagnose the subject.

Furthermore, in some cases, an ultrasound probe including the above-described ultrasound transducer is used to give a treatment to the subject. For example, there is a case where a cautery needle is inserted into the subject for cauterization while the subject is observed by using the ultrasound probe. For this case, there is a known technique in which the difference information between before-treatment information and during-treatment or after-treatment information is visualized so as to monitor the treatment or check a treatment effect (see, for example, Japanese Laid-open Patent Publication No. 2013-128731). In Japanese Laid-open Patent Publication No. 2013-128731, difference information is generated by using before-treatment image information and after-treatment image information, and the difference information is displayed. Examples of the image information in Japanese Laid-open Patent Publication No. 2013-128731 include information obtained by an ultrasound transducer, information obtained by an X-ray computed tomography (CT) apparatus, and information obtained by a magnetic resonance imaging (MRI) apparatus.

SUMMARY

In some embodiments, provided is an ultrasound imaging apparatus that receives an ultrasound signal. The ultrasound imaging apparatus includes a processor including hardware. The processor is configured to: generating first frequency spectrum data and second frequency spectrum data with regard to a first ultrasound signal and a second ultrasound signal, respectively, the second ultrasound signal having a different acquisition time from the first ultrasound signal; generating first ultrasound image data based on the first ultrasound signal; generating second ultrasound image data based on the second ultrasound signal; estimating a displacement amount including at least one of a positional change amount and a rotation angle of a subject depicted in the first ultrasound image data with respect to the subject depicted in the second ultrasound image data; correcting the first frequency spectrum data in accordance with the estimated displacement amount; calculating differential feature data by using the corrected first frequency spectrum data and the second frequency spectrum data; and generating analysis image data to which color information corresponding to the differential feature data is applied.

In some embodiments, provided is a method of operating an ultrasound imaging apparatus that receives an ultrasound signal. The method including: generating first frequency spectrum data and second frequency spectrum data with regard to a first ultrasound signal and a second ultrasound signal, respectively, the second ultrasound signal having a different acquisition time from the first ultrasound signal; generating first ultrasound image data based on the first ultrasound signal; generating second ultrasound image data based on the second ultrasound signal; estimating a displacement amount including at least one of a positional change amount and a rotation angle of a subject depicted in the first ultrasound image data with respect to the subject depicted in the second ultrasound image data; correcting the first frequency spectrum data in accordance with the estimated displacement amount; calculating differential feature data by using the corrected first frequency spectrum data and the second frequency spectrum data; and generating analysis image data to which color information corresponding to the differential feature data is applied.

In some embodiments, provided is a non-transitory computer-readable recording medium having an executable program recorded therein. The program instructs a processor to execute: generating first frequency spectrum data and second frequency spectrum data with regard to a first ultrasound signal and a second ultrasound signal, respectively, the second ultrasound signal having a different acquisition time from the first ultrasound signal; generating first ultrasound image data based on the first ultrasound signal; generating second ultrasound image data based on the second ultrasound signal; estimating a displacement amount including at least one of a positional change amount and a rotation angle of a subject depicted in the first ultrasound image data with respect to the subject depicted in the second ultrasound image data; correcting the first frequency spectrum data in accordance with the estimated displacement amount; calculating differential feature data by using the corrected first frequency spectrum data and the second frequency spectrum data; and generating analysis image data to which color information corresponding to the differential feature data is applied.

In some embodiments, an ultrasound imaging system includes: the ultrasound imaging apparatus; and an ultrasound probe configured to transmit an ultrasound wave to a subject, receive an ultrasound wave backscattered by the subject, and transmit the received ultrasound wave as an ultrasound signal to the ultrasound imaging apparatus.

The above and other features, advantages and technical and industrial significance of this disclosure will be better understood by reading the following detailed description of presently preferred embodiments of the disclosure, when considered in connection with the accompanying drawings.

DETAILED DESCRIPTION

With reference to the accompanying drawings, modes (hereinafter referred to as "embodiments") for carrying out the disclosure are described below.

First Embodiment

Figure 1:
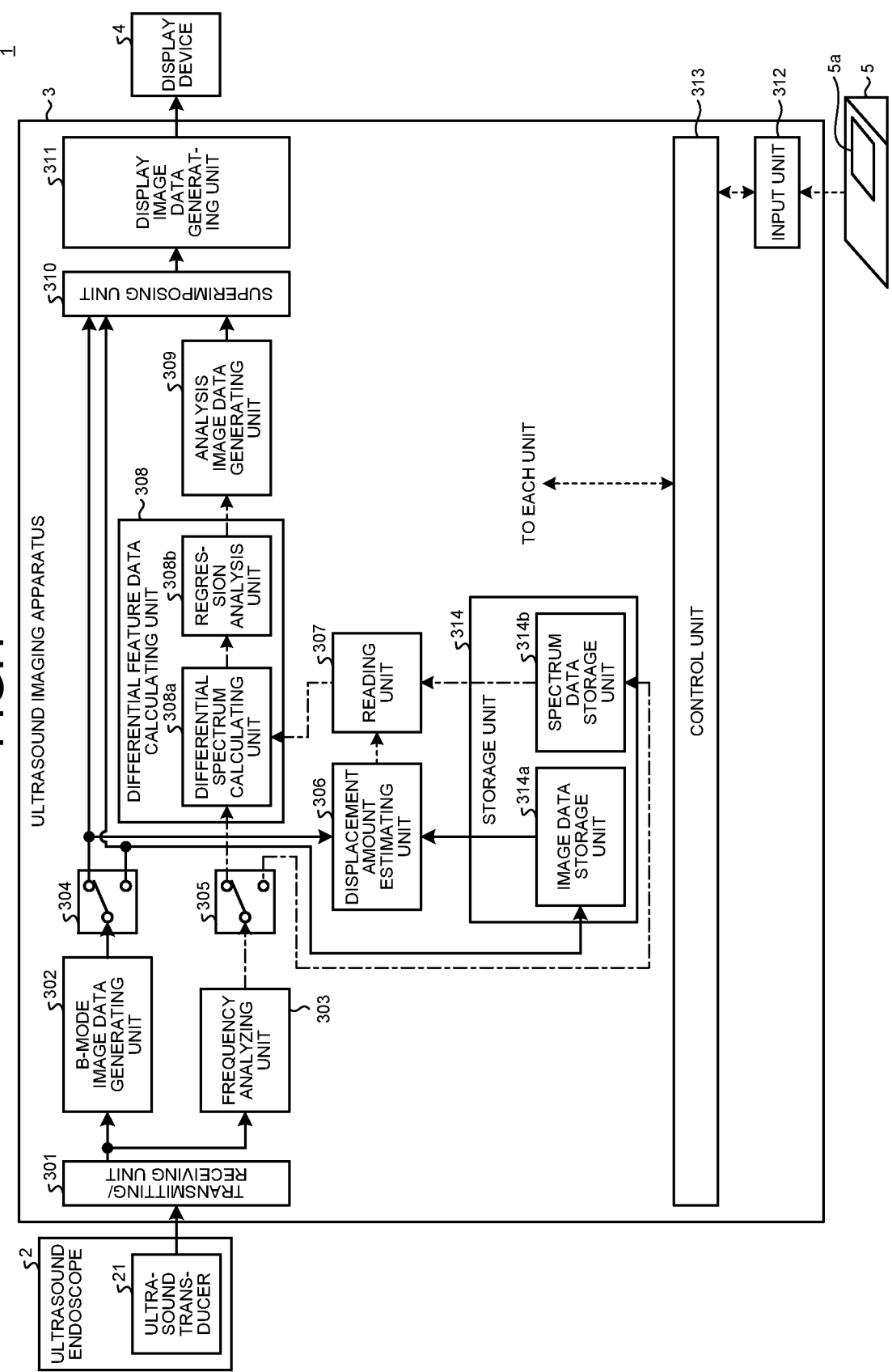
FIG. 1 is a block diagram illustrating a configuration of an ultrasound imaging system including an ultrasound imaging apparatus according to a first embodiment of the disclosure.

FIG. 1 is a block diagram illustrating a configuration of an ultrasound imaging system 1 including an ultrasound imaging apparatus 3 according to a first embodiment of the disclosure. The ultrasound imaging system 1 illustrated in the drawing includes: an ultrasound endoscope 2 that transmits ultrasound waves to a subject and receives the ultrasound waves backscattered by the subject; the ultrasound imaging apparatus 3 that generates an ultrasound image based on an ultrasound signal acquired by the coupled ultrasound endoscope 2; and a display device 4 that displays an ultrasound image generated by the ultrasound imaging apparatus 3. According to the present embodiment, the ultrasound endoscope 2 operates as an ultrasound probe. In the block diagrams described below, a solid arrow denotes the transmission of an electric signal for an image, a dash-dot-dash arrow denotes the transmission of data on a frequency spectrum or feature data, and a dashed arrow denotes the transmission of an electric signal or data for the control, etc.

The ultrasound endoscope 2 includes, in its distal end portion, an ultrasound transducer 21 that converts an electric pulse signal received from the ultrasound imaging apparatus 3 into an ultrasound pulse (acoustic pulse) to emit the ultrasound pulse to the subject and that converts an ultrasound echo backscattered by the subject into an electric echo signal represented by voltage changes.

The ultrasound endoscope 2 includes an elongated insertion unit for the subject. The insertion unit further includes, typically in its distal end portion, an imaging optical system and an imaging element and, when the subject is a tissue inside the human body, is inserted into a gastrointestinal tract (esophagus, stomach, duodenum, or large intestine) or a respiratory tract (trachea or bronchus) to capture a gastrointestinal tract, a respiratory tract, or a peripheral organ (e.g., pancreas, gallbladder, bile duct, biliary tract, lymph node, mediastinal organ, or blood vessel). Further, the insertion unit typically includes a built-in elongated light guide that guides illumination light for illuminating the subject during capturing. The distal end portion of the light guide reaches the distal end of the insertion unit, while the proximal end portion thereof is coupled to a light source device that generates the illumination light.

The ultrasound imaging apparatus 3 includes a transmitting/receiving unit 301, a B-mode image data generating unit 302, a frequency analyzing unit 303, a first switching unit 304, a second switching unit 305, a displacement amount estimating unit 306, a reading unit 307, a differential feature data calculating unit 308, an analysis image data generating unit 309, a superimposing unit 310, a display image data generating unit 311, an input unit 312, a control unit 313, and a storage unit 314.

The transmitting/receiving unit 301 is electrically connected to the ultrasound endoscope 2 to transmit a transmission signal (pulse signal) including a high-voltage pulse to the ultrasound transducer 21 based on a predetermined waveform and transmission timing, receive an echo signal that is an electric high-frequency (radio frequency (RF)) signal from the ultrasound transducer 21, and perform A/D conversion processing described below on the echo signal to generate and output digital data (hereinafter referred to as RF data).

Specifically, the transmitting/receiving unit 301 amplifies a received echo signal. The transmitting/receiving unit 301 performs processing such as filtering on the amplified echo signal and then performs sampling at an appropriate sampling frequency (e.g., 50 MHz) for discretization (what is called A/D conversion processing). Thus, the transmitting/receiving unit 301 generates discretized RF data from the amplified echo signal and outputs the RF data to the B-mode image data generating unit 302 and the frequency analyzing unit 303. When the ultrasound endoscope 2 has a configuration in which the ultrasound transducer 21 having a plurality of elements arranged in an array executes electronical scanning, the transmitting/receiving unit 301 includes a multi-channel circuit for beam synthesis corresponding to the elements.

The frequency band of a pulse signal transmitted by the transmitting/receiving unit 301 is a wide band to cover substantially the linear response frequency band of the ultrasound transducer 21 when the ultrasound transducer 21 performs electroacoustic conversion from a pulse signal into an ultrasound pulse. Further, various processing frequency bands of an echo signal by the transmitting/receiving unit 301 is a wide band to cover substantially the linear response frequency band of the ultrasound transducer 21 when the ultrasound transducer 21 performs acoustoelectric conversion from an ultrasound echo into an echo signal. Thus, when approximate processing of a frequency spectrum is performed as described below, accurate approximation is possible.

Figure 2:
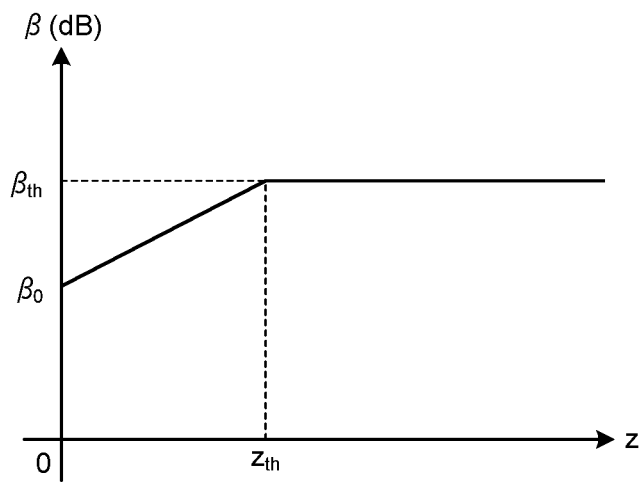
FIG. 2 is a graph illustrating the relationship between a receiving depth and an amplification factor during amplification processing performed by a transmitting/receiving unit.

The B-mode image data generating unit 302 generates B-mode image data based on the RF data received from the transmitting/receiving unit 301. Specifically, the B-mode image data generating unit 302 performs sensitivity time control (STC) correction to amplify the RF data having a large receiving depth with a higher amplification factor. FIG. 2 is a graph illustrating the relationship between a receiving depth and an amplification factor during amplification processing performed by the transmitting/receiving unit 301. FIG. 2 is a logarithmic graph in which the horizontal axis represents a receiving depth z and the vertical axis represents a common logarithm of an amplification factor $\beta$. The unit of the vertical axis is decibel (dB). The receiving depth z illustrated in FIG. 2 is the value calculated based on the elapsed time after an ultrasound wave starts to be received. On the logarithmic graph illustrated in FIG. 2, the amplification factor $\beta$ increases linearly from $\beta_0$ to $\beta_{th}$ ($>\beta_0$) in accordance with an increase in the receiving depth z when the receiving depth z is smaller than a threshold $z_{th}$. The amplification factor $\beta$ is the constant value $\beta_{th}$ when the receiving depth z is equal to or more than the threshold $z_{th}$. The value of the threshold $z_{th}$ is a value such that most of the ultrasound signal received from the subject has attenuated and a noise has become dominant. Furthermore, the storage unit 314 previously stores the relationship illustrated in FIG. 2.

Further, the B-mode image data generating unit 302 applies a bandpass filter or envelope detection to the RF data to generate the data indicating the amplitude or the intensity of an echo signal. Subsequently, the B-mode image data generating unit 302 performs known processing such as logarithmic conversion on the data to generate digital sound ray data. During the logarithmic conversion, the data indicating the amplitude or the intensity of an echo signal is converted by being divided by a specific voltage $V_c$, which is called a reference voltage, and then obtaining the common logarithm thereof. The converted data is represented by using a decibel value. The sound ray data is data in which the value proportional to the digit representing, as a decimal digit, the amplitude or the intensity of the echo signal indicating the intensity of backscattering of an ultrasound pulse is arranged along the transmitting/receiving direction (depth direction) of the ultrasound pulse.

Figure 3:
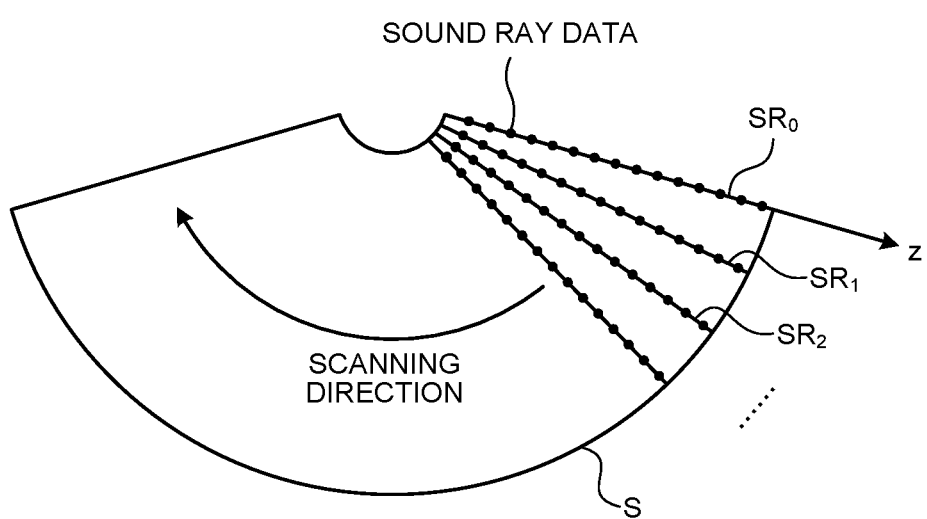
FIG. 3 is a diagram schematically illustrating a scan region of an ultrasound transducer and sound ray data.

FIG. 3 is a diagram schematically illustrating a scan region of the ultrasound transducer 21 (hereinafter also simply referred to as a scan region) and sound ray data. A scan region S illustrated in FIG. 3 is shaped like a fan. In FIG. 3, the path (sound ray) in which an ultrasound wave from the ultrasound transducer 21 reciprocates is represented as a straight line and sound ray data is represented as a point located on each sound ray. In FIG. 3, for convenience of the subsequent description, the respective sound rays are denoted by the numbers 1, 2, 3, . . . , in order from the start of scanning (right in FIG. 3), and a first sound ray is defined as $SR_1$, a second sound ray as $SR_2$, a third sound ray as $SR_3$, . . . , and a k-th sound ray as $SR_k$. FIG. 3 corresponds to a case where the ultrasound transducer 21 is a convex transducer. Furthermore, in FIG. 3, the receiving depth of sound ray data is described as z. When an ultrasound pulse emitted from the surface of the ultrasound transducer 21 is backscattered inside an object in the receiving depth z and returned to the ultrasound transducer 21 as an ultrasound echo, the relationship between a reciprocation distance L and the receiving depth z is $z=L/2$.

Further, the B-mode image data generating unit 302 performs signal processing using a known technique such as gain processing or contrast processing on sound ray data.

The B-mode image data generating unit 302 performs coordinate conversion to rearrange sound ray data such that the generated sound ray data may express the spatially proper scan region, and then performs an interpolation process on sets of sound ray data to fill the gap between the sets of sound ray data so as to generate B-mode image data. The B-mode image is a gray-scale image in which the values of R (red), G (green), and B (blue), which are variables when the RGB color system is used as a color space, are matched to each other. The B-mode image data generating unit 302 outputs the generated B-mode image data to the first switching unit 304.

The frequency analyzing unit 303 performs fast Fourier transform (FFT) on the RF data generated by the transmitting/receiving unit 301 to perform frequency analysis so as to calculate data of a frequency spectrum. Specifically, the frequency analyzing unit 303 divides the RF data (line data) of each sound ray generated by the transmitting/receiving unit 301 into multiple portions at a predetermined relatively short time interval and performs FFT processing on the RF data (hereinafter referred to as "RF data string") of each divided portion so as to calculate the frequency spectrum in each portion of the sound ray. The term "frequency spectrum" refers to "the frequency distribution of the intensity or the voltage amplitude of an echo signal obtained in the certain receiving depth z (i.e., the certain reciprocation distance L)" obtained by performing FFT processing on an RF data string.

In the case described according to the first embodiment, the frequency distribution of the voltage amplitude of an echo signal is used as a frequency spectrum. In the case described, for example, the frequency analyzing unit 303 generates data of a frequency spectrum (hereinafter also referred to as frequency spectrum data) based on a frequency component V(f, L) of the voltage amplitude. f is a frequency. The frequency analyzing unit 303 divides the frequency component V(f, L) of the amplitude of the RF data (actually, the voltage amplitude of the echo signal) by the reference voltage $V_c$, obtain a common logarithm (log), and makes representation by using a decibel as a unit so as to perform logarithmic conversion processing and then executes multiplication by an appropriate positive constant α to generate frequency spectrum data S(f, L) of the subject as represented by the following Equation (1).

$$S(f,L)=\alpha \cdot \log\{V(f,L)/V_c\} \quad (1)$$

A method of obtaining the frequency component V(f, L) of the voltage amplitude during the frequency analysis by the frequency analyzing unit 303 is described below in detail. Generally, the frequency spectrum of an echo signal exhibits a different tendency depending on the characterization of the human tissue scanned by the ultrasound wave when the subject is a human tissue. This is because the frequency spectrum has a correlation with the size, the number density, the acoustic impedance, and the like, of a scatterer that scatters an ultrasound wave. The term "characterization of the human tissue" refers to the characteristic of the tissue, such as malignant tumor (cancer), benign tumor, endocrine tumor, mucinous tumor, normal tissue, cyst, or vascular channel.

Figure 4:
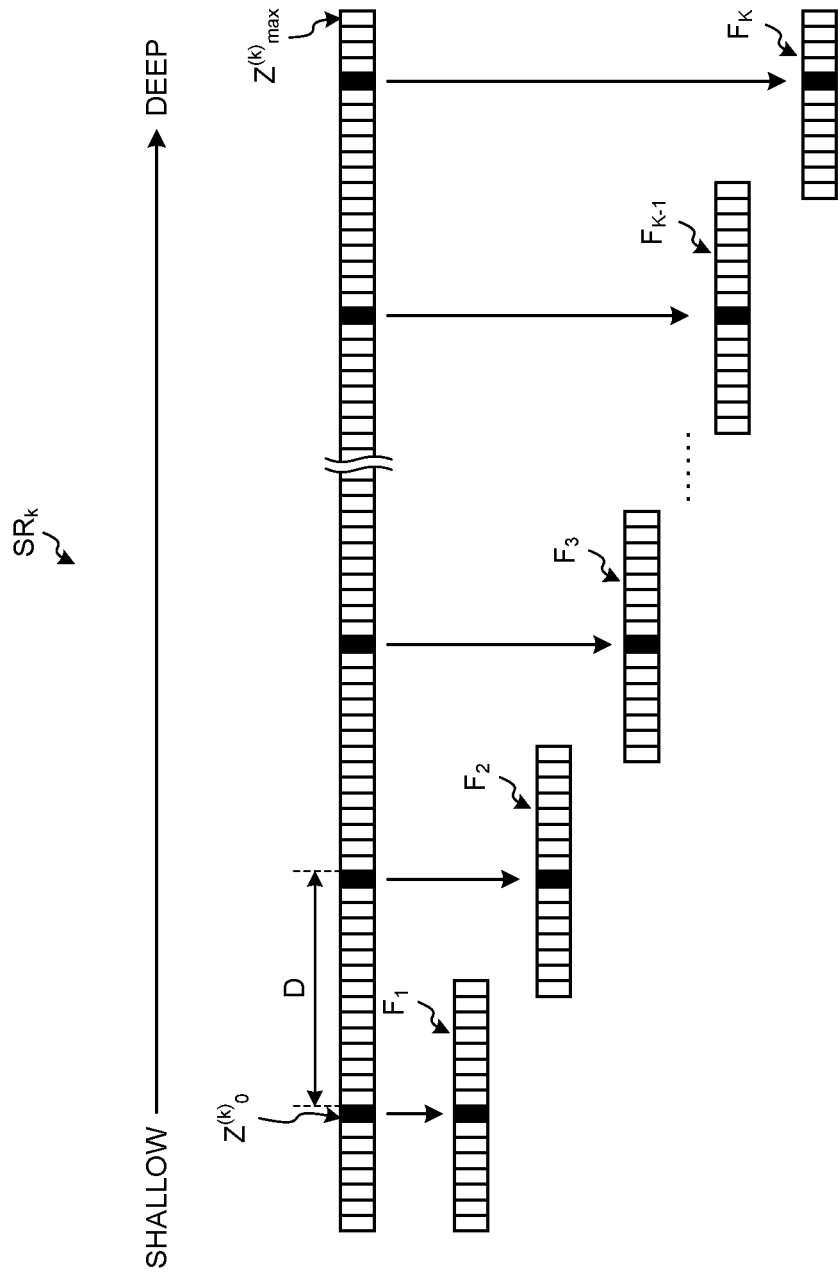
FIG. 4 is a diagram schematically illustrating data array in RF data on a single sound ray of an ultrasound signal.

FIG. 4 is a diagram schematically illustrating data array in RF data on the single sound ray $SR_k$ of an ultrasound signal. A rectangle indicated in white or black in the sound ray $SR_k$ represents the data at one sample point. In the RF data on the sound ray $SR_k$, the data located closer to the right side is the RF data in a deeper point measured along the sound ray $SR_k$ from the ultrasound transducer 21 (see the arrow in FIG. 4). As described above, the RF data on the sound ray $SR_K$ is RF data obtained by being sampled from the echo signal during the A/D conversion processing by the transmitting/receiving unit 301 so as to be discretized. In the case described in FIG. 4, the position of the eighth data in the RF data on the sound ray $SR_k$ with the number k is set as an initial value $Z^{(k)}_0$ in the direction of the receiving depth z; however, the position of the initial value may be optionally set. A calculation result by the frequency analyzing unit 303 is obtained as a complex number and is stored in the storage unit 314.

An RF data string $F_j$ (j=1, 2, . . . , K) illustrated in FIG. 4 is a portion that is included in the RF data and is the target for FFT processing. Generally, in order to perform FFT processing, an RF data string needs to have the number of sets of data that is a power of 2. In this sense, the RF data string $F_j$ (j=1, 2, . . . , K−1) except for $F_K$ has the number of sets of data of 16 (=$2^4$) and is a proper RF data string. On the other hand, the RF data string $F_K$ has the number of sets of data of 12 and is an improper RF data string. When FFT processing is performed on an improper RF data string, a process is performed to insert zero data corresponding to a shortage so as to generate a proper RF data string. This point is described in detail when a process of the frequency analyzing unit 303 is described (see FIG. 13). Subsequently, as described above, the frequency analyzing unit 303 performs FFT processing, calculates the frequency component V(f, L) of the voltage amplitude, and calculates the frequency spectrum data S(f, L) based on the above-described Equation (1). The frequency analyzing unit 303 further repeatedly performs this operation on all the sound rays illustrated in FIG. 3 to calculate the frequency spectrum data S(f, L) in all directions and outputs the frequency spectrum data S(f, L) to the second switching unit 305 (hereinafter, the "direction" is referred to as the direction to which each sound ray data is oriented across all the scanning directions in FIG. 3).

The first switching unit 304 switches the transmission path of the B-mode image data generated by the B-mode image data generating unit 302 under the control of the control unit 313. Specifically, the first switching unit 304 selectively outputs B-mode image data to the displacement amount estimating unit 306 and the superimposing unit 310 or the superimposing unit 310 and the storage unit 314 (an image data storage unit 314a described below).

The second switching unit 305 switches the transmission path of the frequency spectrum data generated by the frequency analyzing unit 303 under the control of the control unit 313. Specifically, the second switching unit 305 selectively outputs frequency spectrum data to the differential feature data calculating unit 308 or the storage unit 314 (a spectrum data storage unit 314b described below).

The displacement amount estimating unit 306 estimates the subject or at least a part thereof depicted in the image by using two sets of B-mode image data acquired from the identical subject at different times. For example, the displacement amount of a blood vessel or a tumor is estimated as the subject or a part thereof. The displacement amount estimating unit 306 estimates the displacement amount of the identical subject at different times, for example, the subject before cauterization and during cauterization. The displacement amount estimated by the displacement amount estimating unit 306 includes the displacement distance of a B-mode image in the horizontal direction and in the vertical direction and the rotation angle of the image. Although the present embodiment is described by using the image and the frequency spectrum data before cauterization and various images and various types of data during cauterization, after-cauterization images or data may be used instead of during-cauterization images or data as long as the images and the data are acquired after the before-cauterization images and data.

Figure 5:
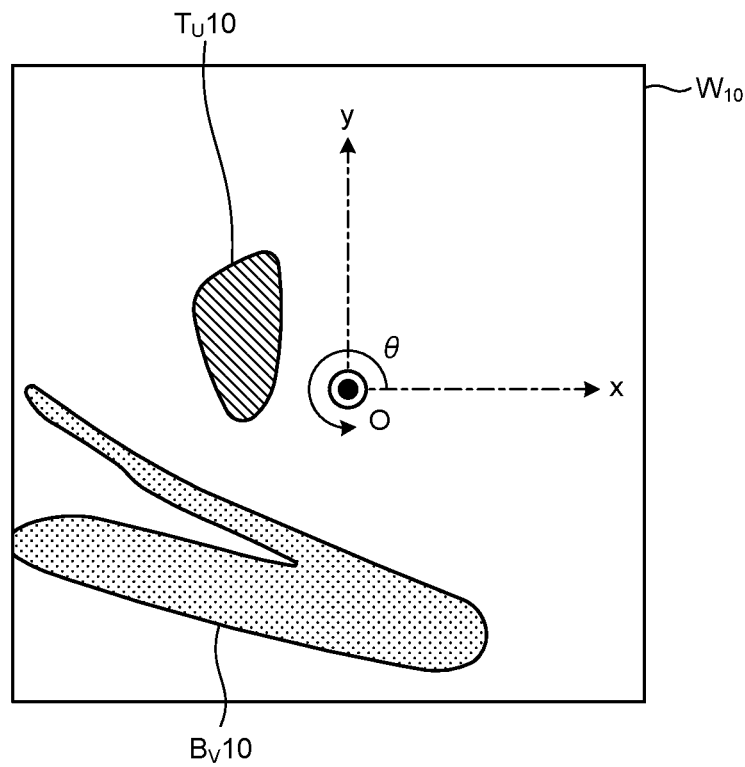
FIG. 5 is a diagram illustrating an example of a B-mode image before cauterization with a cautery needle.
Figure 6:
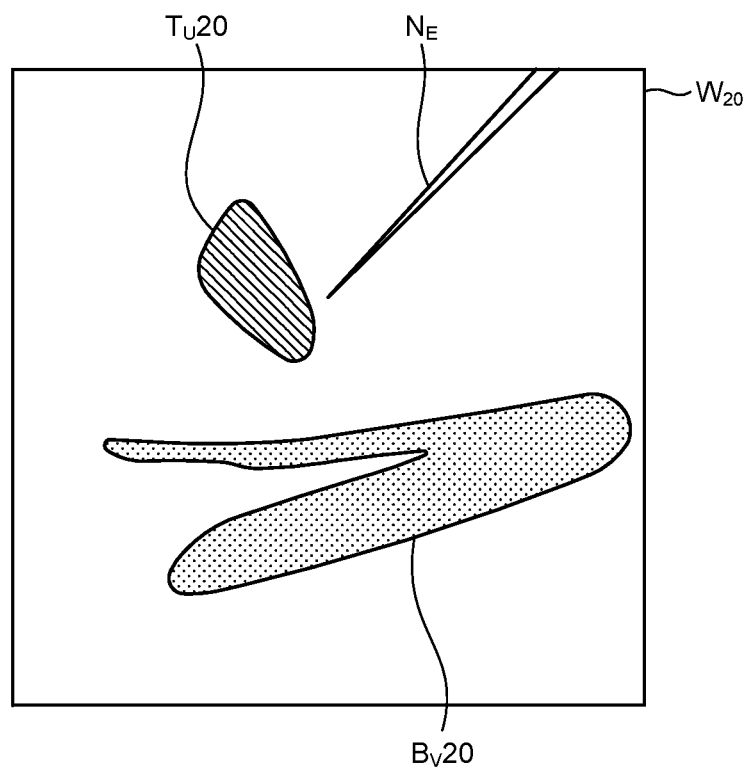
FIG. 6 is a diagram illustrating an example of a B-mode image during cauterization with the cautery needle.

FIG. 5 is a diagram illustrating an example of a B-mode image before cauterization with a cautery needle. FIG. 6 is a diagram illustrating an example of a B-mode image during cauterization with the cautery needle. A blood vessel (a blood vessel image $B_V10$) and a tumor (a tumor image $T_U10$) are depicted in a B-mode image $W_{10}$ illustrated in FIG. 5. Furthermore, a blood vessel (a blood vessel image $B_V20$), a tumor (a tumor image $T_U20$), and a cautery needle (a cautery needle image $N_E$) are depicted in a B-mode image $W_{20}$ illustrated in FIG. 6. The description below uses the coordinate system in which the horizontal direction of the B-mode image is in an x-direction, the vertical direction thereof is in a y-direction, an image center O is the origin, and the rotation around the image center O in the direction of θ in FIG. 5 is possible. Moreover, in the illustration of FIG. 5, the coordinate system O-xy is virtually superimposed on the B-mode image $W_{10}$.

The displacement amount estimating unit 306 estimates how the blood vessel image $B_V10$ and the tumor image $T_U10$ (see FIG. 5) of the before-cauterization B-mode image $W_{10}$ have been displaced with respect to the blood vessel image $B_V20$ and the tumor image $T_U20$ (see FIG. 6) of the during-cauterization B-mode image $W_{20}$. Specifically, the displacement amount estimating unit 306 executes coordinate conversion including at least any one of the displacement in the x-direction, the displacement in the y-direction, and/or the rotation around the origin on the before-cauterization B-mode image $W_{10}$ while calculating the correlation value between the B-mode image $W_{10}$ (strictly, a B-mode image $W_{11}$ described below) having undergone the coordinate conversion and the B-mode image $W_{20}$. In the description below, at least any one of a position change $\Delta x$ in the x-direction, a position change $\Delta y$ in the y-direction, and an angular change (a rotation angle $\Delta\theta$) of the rotation of the B-mode image $W_{10}$ is simply a "displacement amount". The displacement amount used for the estimation by the displacement amount estimating unit 306 may be various displacement amounts that change by a previously set range, a displacement amount having a previously set pattern, or a displacement amount set by an input of an operator via a keyboard 5.

Figure 7:
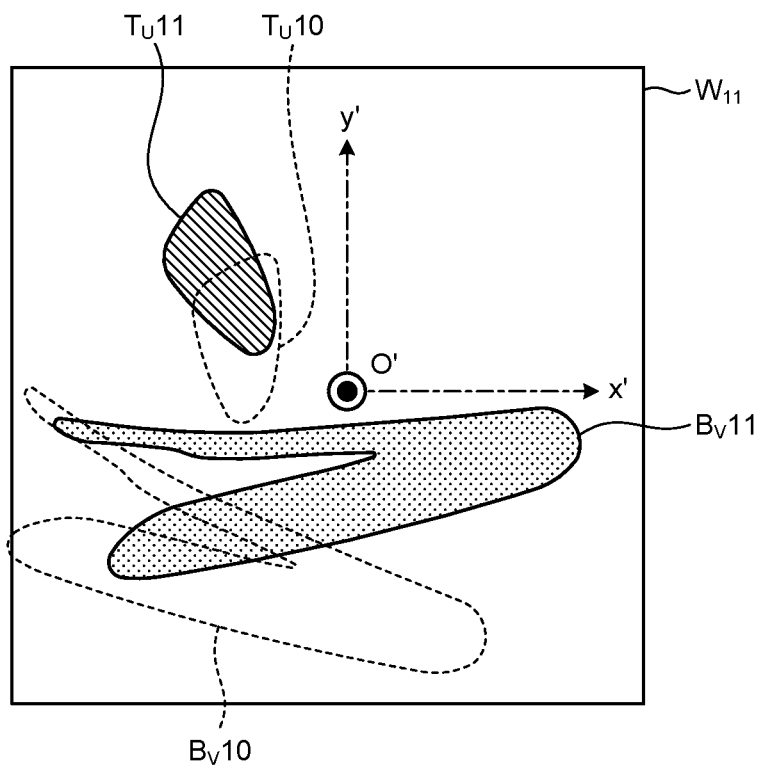
FIG. 7 is a diagram illustrating a B-mode image.

The displacement amount estimating unit 306 rotates the before-cauterization B-mode image $W_{10}$ illustrated in FIG. 5 by the rotation angle $\Delta\theta$ and then moves the B-mode image $W_{10}$ by $\Delta x$ in the horizontal direction and by $\Delta y$ in the vertical direction to execute coordinate conversion so as to obtain the B-mode image $W_{11}$. FIG. 7 is a diagram illustrating the B-mode image $W_{11}$. For the convenience of description, a coordinate system O'-x'y' is virtually superimposed on the illustration in FIG. 7. The luminance at a given point (x, y) of the B-mode image $W_{10}$ in FIG. 5 is represented as a two-variable function $P_1(x, y)$, and the luminance at a given point (x', y') in the B-mode image $W_{11}$ in FIG. 7 is represented as a two-variable function $P_1'(x', y')$. Here, the following Equations (2) and (3) are satisfied.

$$P_1'(x', y') = P_1(x, y) \quad (2)$$

$$\begin{pmatrix} x' \\ y' \end{pmatrix} = \begin{pmatrix} \cos(\Delta\theta) & -\sin(\Delta\theta) \\ \sin(\Delta\theta) & \cos(\Delta\theta) \end{pmatrix} \begin{pmatrix} x \\ y \end{pmatrix} + \begin{pmatrix} \Delta x \\ \Delta y \end{pmatrix} \quad (3)$$

Figure 8:
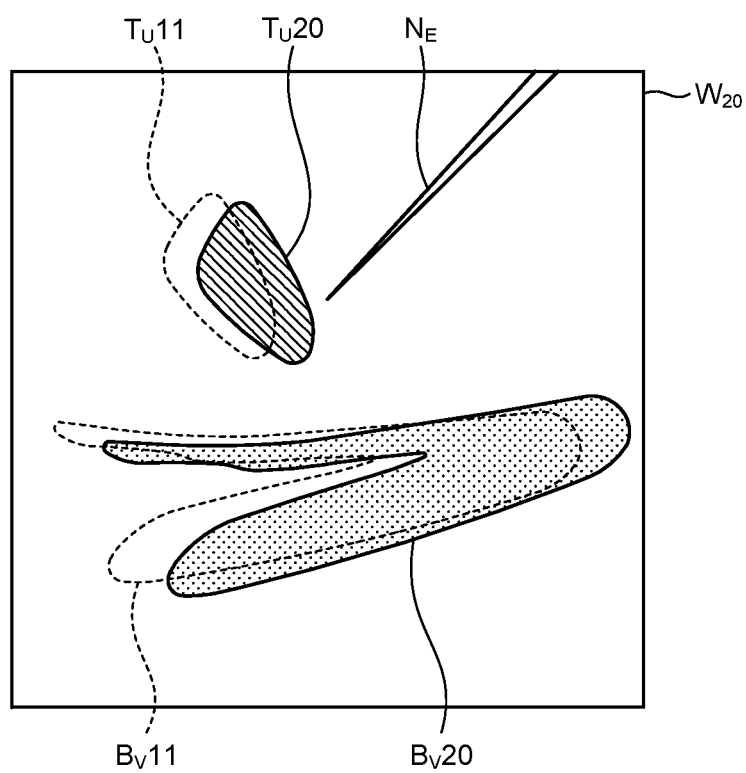
FIG. 8 is a diagram illustrating the location of a blood vessel and a tumor in the during-cauterization B-mode image illustrated in FIG. 6 and in the before-cauterization B-mode image having undergone coordinate conversion illustrated in FIG. 7.

FIG. 8 is a diagram illustrating the location of a blood vessel and a tumor in the during-cauterization B-mode image $W_{20}$ illustrated in FIG. 6 and in the before-cauterization B-mode image $W_{11}$ having undergone the coordinate conversion illustrated in FIG. 7. The displacement amount estimating unit 306 calculates the correlation value between the before-cauterization B-mode image $W_{11}$, which has undergone the coordinate conversion, and the during-cauterization B-mode image $W_{20}$. Furthermore, the displacement amount ($\Delta x$, $\Delta y$, $\Delta\theta$) (with regard to the order of the coordinate conversion, the rotation by the rotation angle $\Delta\theta$ comes first) includes a case in which all of the displacement amounts are zero, that is, there is no displacement.

The brightness at the given point (x', y') of the B-mode image $W_{20}$ in FIG. 8 is represented by a two-variable function $P_2(x', y')$. A correlation value $C_V(\Delta x, \Delta y, \Delta\theta)$ between a value $P_1'(x', y')$ of the B-mode image $W_{11}$ having undergone the coordinate conversion by the displacement amount ($\Delta x$, $\Delta y$, $\Delta\theta$) by the displacement amount estimating unit 306 and a value $P_2(x', y')$ of the B mode image $W_{20}$ is defined by the following Equation (4).

$$C_V(\Delta x, \Delta y, \Delta\theta) = \iint P_1'(x', y') \cdot P_2(x', y') dx' dy' \quad (4)$$

Equation (2) is substituted into Equation (4) to obtain the following Equation (5). Here, both x and y are expressed as two-variable functions x(x', y') and y(x', y') of x' and y', respectively.

$$C_V(\Delta x, \Delta y, \Delta\theta) = \iint P_1(x(x', y'), y(x', y')) \cdot P_2(x', y') dx' dy' \quad (5)$$

Here, Equation (3) is calculated back for x(x', y') and y(x', y') to obtain the following Equation (6).

$$\begin{pmatrix} x(x', y') \\ y(x', y') \end{pmatrix} = \begin{pmatrix} \cos(\Delta\theta) & \sin(\Delta\theta) \\ -\sin(\Delta\theta) & \cos(\Delta\theta) \end{pmatrix} \begin{pmatrix} x' - \Delta x \\ y' - \Delta y \end{pmatrix} \quad (6)$$

The displacement amount estimating unit 306 substitutes various values as the displacement amount ($\Delta x$, $\Delta y$, $\Delta\theta$) into the right side of Equation (6) and substitutes the calculation results x(x', y') and y(x', y') into the right side of Equation (5) to calculate various values of the correlation value $C_V(\Delta x, \Delta y, \Delta\theta)$. In general, the calculation of Equation (5) is called cross-correlation, and the correlation value $C_V$ becomes maximum when the B-mode image $W_{11}$ and the B-mode image $W_{20}$ have the matching position and direction. Although the integral symbol $\int$ is used in Equation (5) and Equation (4), the displacement amount estimating unit 306 actually performs an operation to calculate the product sum of the luminance values of discrete pixels.

The displacement amount estimating unit 306 specifies the displacement amount ($\Delta x_0$, $\Delta y_0$, $\Delta\theta_0$) that gives a maximum value $\max C_V$ among the calculated various correlation values $C_V(\Delta x, \Delta y, \Delta\theta)$. Then, the displacement amount estimating unit 306 outputs the displacement amount ($\Delta x_0$, $\Delta y_0$, $\Delta\theta_0$) to the reading unit 307 as the estimated displacement amount of the subject from before cauterization (the blood vessel image $B_V10$ and the tumor image $T_U10$) until during cauterization (the blood vessel image $B_V20$ and the tumor image $T_U20$). When there is no displacement of the subject between the before-cauterization B-mode image and the during-cauterization B-mode image, the estimated displacement amount is zero.

The storage unit 314 (the spectral data storage unit 314b) stores the frequency spectrum data S(f, L) acquired before cauterization and calculated for all the directions and all the depths z (=L/2).

The reading unit 307 reads the frequency spectrum data S(f, L) acquired before cauterization with regard to all the directions and the depths from the storage unit 314 (the spectral data storage unit 314b) and executes coordinate conversion by the displacement amount estimated by the displacement amount estimating unit 306 with respect to Cartesian coordinates x and y defined by the direction and the depth of S(f, L). The reading unit 307 outputs the frequency spectrum data having undergone the coordinate conversion to the differential feature data calculating unit 308. The reading unit 307 functions as a correcting unit that corrects the before-cauterization frequency spectrum data in accordance with the during-cauterization frequency spectrum data.

The differential feature data calculating unit 308 calculates differential feature data based on the during-cauterization frequency spectrum data calculated by the frequency analyzing unit 303 and the before-cauterization frequency spectrum data acquired from the reading unit 307 and having undergone coordinate conversion. The differential feature data calculating unit 308 includes a differential spectrum calculating unit 308a and a regression analysis unit 308b.

Figure 9:
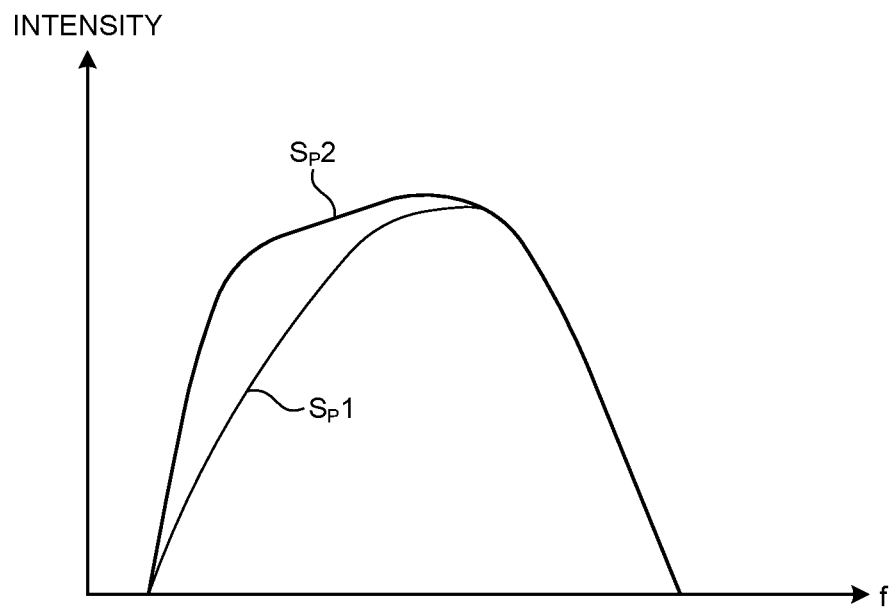
FIG. 9 is a graph illustrating an example of a before-cauterization frequency spectrum and a during-cauterization frequency spectrum calculated by a frequency analyzing unit.

The differential spectrum calculating unit 308a subtracts the before-cauterization frequency spectrum data having undergone coordinate conversion from the during-cauterization frequency spectrum data with the direction and the depth, the Cartesian coordinates defined by the direction and the depth, and the frequency matched to each other. Then, the differential spectrum calculating unit 308a calculates the differential spectrum data having undergone the subtraction. FIG. 9 is a graph illustrating an example of the before-cauterization frequency spectrum and the during-cauterization frequency spectrum calculated by the frequency analyzing unit 303. The differential spectrum calculating unit 308a calculates, for example, the difference between frequency spectrum data $S_P2$ obtained during cauterization and frequency spectrum data $S_P1$ obtained before cauterization with regard to each frequency to calculate differential spectrum data.

Figure 10:
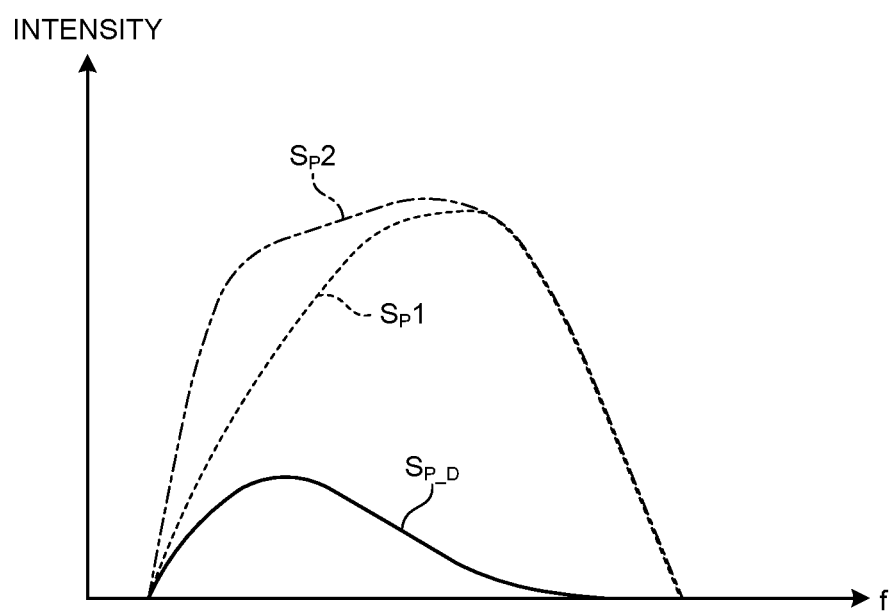
FIG. 10 is a graph illustrating differential spectrum data between frequency spectrum data calculated from before-cauterization RF data and frequency spectrum data calculated from during-cauterization RF data.

FIG. 10 is a graph illustrating differential spectrum data $S_{P\_D}$ between the frequency spectrum data $S_P1$ calculated from the before-cauterization RF data and the frequency spectrum data $S_P2$ calculated from the during-cauterization RF data. The differential spectrum calculating unit 308a calculates the difference between the during-cauterization frequency spectrum data $S_P2$ and the before-cauterization frequency spectrum data $S_P1$ to generate the differential spectrum data $S_{P\_D}$ illustrated in FIG. 10. The differential spectrum calculating unit 308a calculates differential spectrum data with regard to each of all the directions and each of all the depths.

The regression analysis unit 308b approximates multiple sets of differential spectrum data output from the differential spectrum calculating unit 308a with a straight line, calculates feature data (hereinafter referred to as differential feature data) of the differential spectrum data by using the straight line, and outputs the differential feature data to the analysis image data generating unit 309.

Specifically, the regression analysis unit 308b executes single regression analysis on the frequency spectrum data in a predetermined frequency band to approximate the frequency spectrum data with a linear expression (regression line) so as to calculate differential feature data that defines the approximated linear expression. The single regression analysis is the regression analysis in a case where there is only one type of independent variable. The independent variable for the single regression analysis according to the present embodiment correspond to the frequency f.

Figure 11:
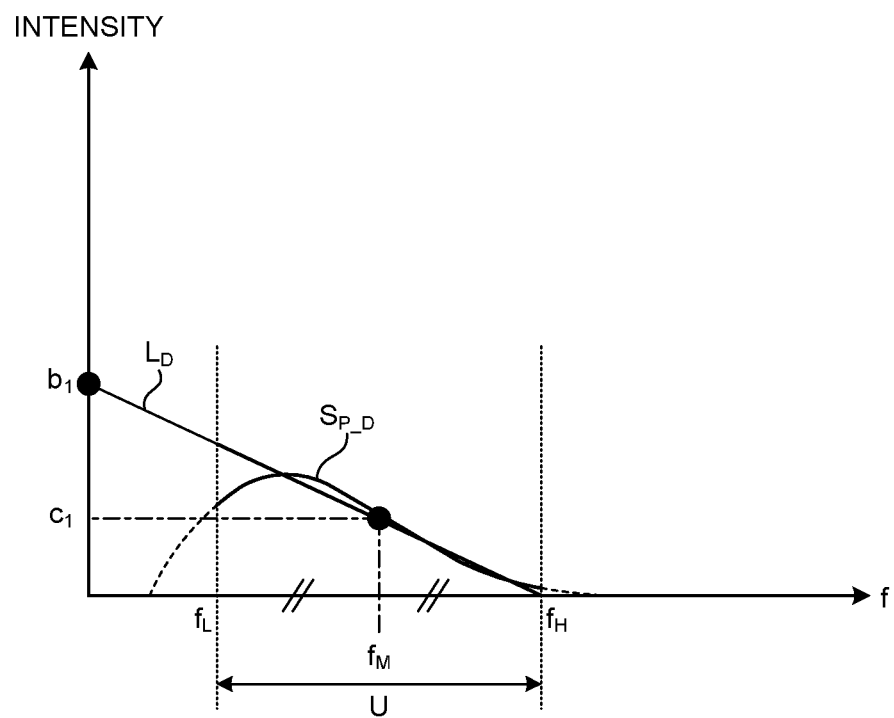
FIG. 11 is a graph illustrating the calculation of differential feature data executed by a regression analysis unit according to the first embodiment of the disclosure.

FIG. 11 is a graph illustrating the calculation of differential feature data executed by the regression analysis unit 308b according to the first embodiment of the disclosure. For example, the regression analysis unit 308b executes single regression analysis in a frequency band U to obtain a regression line $L_D$ of the difference spectral data $S_{P\_D}$. Then, the regression analysis unit 308b calculates, as differential feature data, a slope $a_1$ and an intercept $b_1$ of the regression line $L_D$ and a mid-band fit $c_1 = a_1 f_M + b_1$ that is a value on the regression line at the center frequency (i.e., "mid-band") $f_M = (f_L + f_M)/2$ of the frequency band U. As the differential spectrum data $S_{P\_D}$ is expressed by using the parameters (the slope $a_1$, the intercept $b_1$, and the mid-band fit $c_1$) of the linear expression that defines the regression line $L_D$ as described above, the differential spectrum data $S_{P\_D}$ is approximated to a linear expression.

It is considered that, among the three sets of differential feature data calculated from the frequency spectrum data, the slope $a_1$ and the intercept $b_1$ have a correlation with the size of a scatterer that scatters an ultrasound wave, the scattering intensity of a scatterer, the number density (concentration) of a scatterer, etc. The mid-band fit $c_1$ provides the voltage magnitude and the intensity of an echo signal at the center of the effective frequency band. Therefore, it is considered that the mid-band fit $c_1$ has a certain degree of correlation with the luminance of a B-mode image in addition to the size of a scatterer, the scattering intensity of a scatterer, and the number density of a scatterer. Furthermore, the regression analysis unit 308b may execute regression analysis to approximate frequency spectrum data with a second- or higher-order polynomial.

With reference back to FIG. 1, the analysis image data generating unit 309 generates the analysis image data to which the visual information corresponding to the differential feature data calculated by the differential feature data calculating unit 308 is applied. Specifically, the analysis image data generating unit 309 generates the analysis image data in which the visual information associated with the differential feature data calculated by the regression analysis unit 308b is assigned to each corresponding pixel position of the image in the B-mode image data. Examples of the visual information include variables in a color space forming a predetermined color system, such as hue, saturation, brightness, luminance value, R (red), G (green), or B (blue). Then, the analysis image data generating unit 309 assigns the visual information associated with the differential feature data calculated from the single RF data string $F_j$ (j=1, 2, . . . , and K) illustrated in FIG. 4 to the pixel region defined by, for example, the depth length proportional to the data amount of the RF data string $F_j$ and the direction interval between the sound rays illustrated in FIG. 3.

Here, the frequency analyzing unit 303, the differential feature data calculating unit 308, and the analysis image data generating unit 309 may limit the analysis range to the region of interest (ROI) that is divided by, for example, a specific depth range and direction range (i.e., a range in the scanning direction) in the scan region S illustrated in FIG. 3 to perform each of the above-described processes. Limiting the region of interest to a necessary region makes it possible to reduce the amount of calculation and improve the speed for the display.

The superimposing unit 310 synthesizes the analysis image data generated by the analysis image data generating unit 309 with the B-mode image data generated by the B-mode image data generating unit 302 to generate superimposition image data.

The display image data generating unit 311 performs, on the superimposition image data generated by the superimposing unit 310 or the B-mode image data, predetermined processing such as gradation processing or data decimation corresponding to the display range of an image on the display device 4 and then causes the display device 4 to display the data.

The input unit 312 generates the selection signal including the information on the key or the menu that has been selected and input in accordance with the operation signal from the keyboard 5 and outputs the selection signal to the control unit 313.

Here, the keyboard 5 is configured by using a plurality of buttons to enable the input of various types of information so as to receive the input from an operator. Further, the keyboard 5 includes a touch panel 5a including a display screen. The touch panel 5a receives, for example, the input corresponding to the contact position of the finger of the operator. Then, the keyboard 5 outputs, to the input unit 312, the operation signal including the position (coordinates) of the touch (contact) by the operator in accordance with the operation icon displayed on the display screen of the touch panel 5a, the button number for identifying the button whose input has been made, and the like. Moreover, the touch panel 5a displays ultrasound images and various types of information so as to function as a graphical user interface (GUI). The touch panel may be a resistive type, a capacitance type, an optical type, or the like, and any type of touch panel may be used.

The control unit 313 reads, from the storage unit 314, information such as an operation program saved and stored in the storage unit 314, operation parameters and data for each process, and the like, and executes various calculation processes related to the method of operating the ultrasound imaging apparatus 3 so as to control the ultrasound imaging apparatus 3 in an integrated manner.

The transmitting/receiving unit 301, the B-mode image data generating unit 302, the frequency analyzing unit 303, the first switching unit 304, the second switching unit 305, the displacement amount estimating unit 306, the reading unit 307, the differential feature data calculating unit 308, the analysis image data generating unit 309, the superimposing unit 310, the display image data generating unit 311, the input unit 312, and the control unit 313, which are described above, are configured by using, for example, a general-purpose processor such as a central processing unit (CPU) having arithmetic and control functions or a dedicated integrated circuit that performs a specific function such as an application specific integrated circuit (ASIC) or a field programmable gate array (FPGA). Multiple units including at least a part of the above-described units including the control unit 313 and the B-mode image data generating unit 302 may be configured by using a common general-purpose processor, a dedicated integrated circuit, etc.

The storage unit 314 stores arithmetic parameters, data, and the like, for each process. The storage unit 314 includes an image data storage unit 314a that stores B-mode image data generated by the B-mode image data generating unit 302 and the above-described spectrum data storage unit 314b that stores frequency spectrum data calculated by the frequency analyzing unit 303. The storage unit 314 is configured by using, for example, a hard disk drive (HDD).

Further, in addition to the above-described information, the storage unit 314 stores, for example, the information necessary for amplification processing (the relationship between the amplification factor and the receiving depth illustrated in FIG. 2), the information necessary for logarithmic conversion processing (see Equation (1), for example, the values of a and $V_c$), and the information on a window function (Hamming, Hanning, Blackman, etc.) necessary for frequency analysis processing.

Further, the storage unit 314 includes, as an additional memory, a non-transitory computer-readable recording medium, e.g., a read only memory (ROM) (not illustrated), in which the operation program for implementing the method of operating the ultrasound imaging apparatus 3 is previously installed. The operation program may be widely distributed by being recorded in a computer-readable recording medium, such as a portable hard disk, a flash memory, a CD-ROM, a DVD-ROM, or a flexible disk. Moreover, the above-described various programs may be acquired by being downloaded via a communication network. The communication network described here is configured by using, for example, an existing public line network, a LAN, or a WAN and may be wired or wireless.

Figure 12:
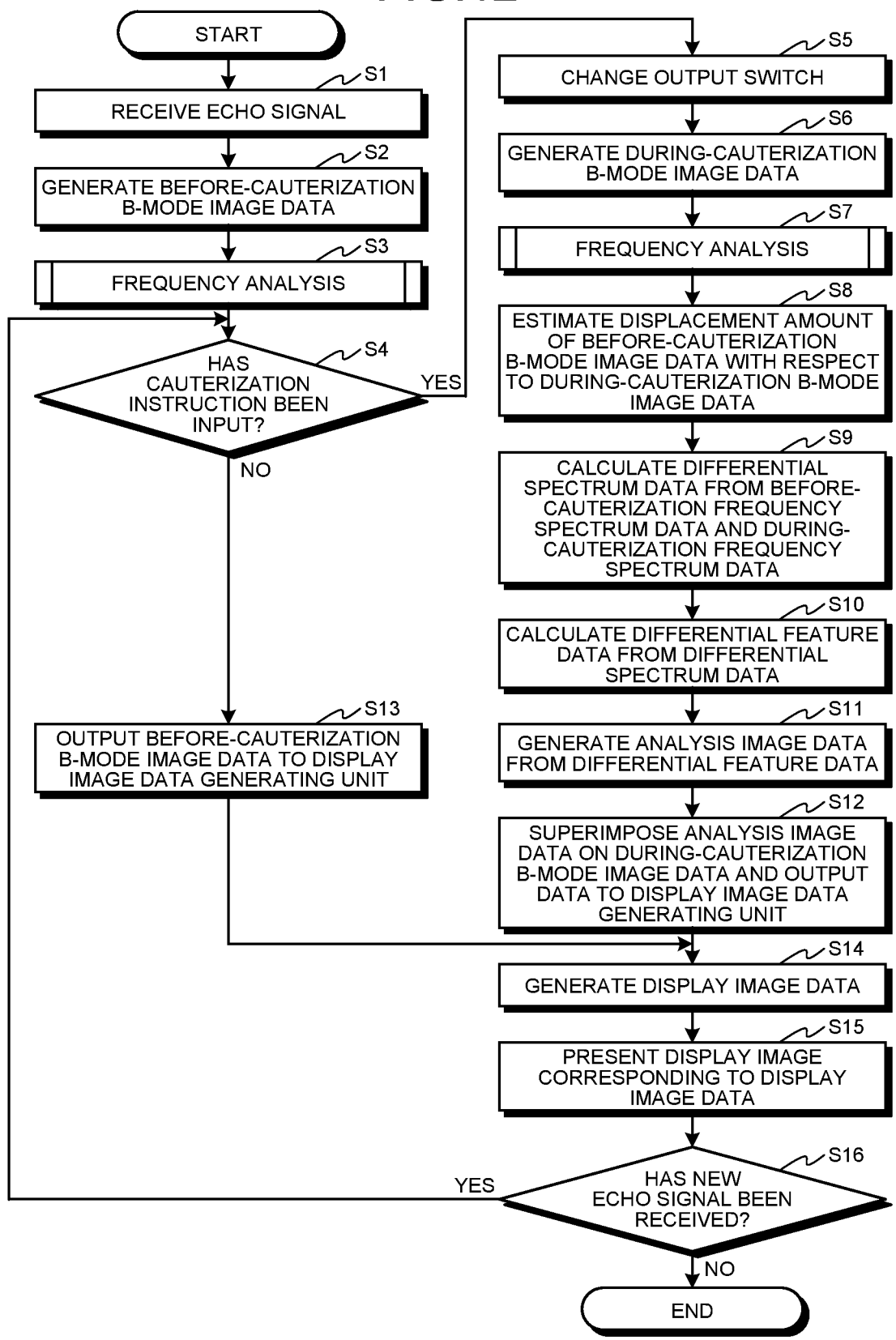
FIG. 12 is a flowchart illustrating the overview of a process performed by the ultrasound imaging apparatus according to the first embodiment of the disclosure.

FIG. 12 is a flowchart illustrating the overview of a process performed by the ultrasound imaging apparatus 3 having the above-described configuration. In the description below, it is assumed that each unit is operated under the control of the control unit 313. In the default settings, the respective outputs of the first switching unit 304 and the second switching unit 305 are in contact with the respective lower right terminals illustrated in FIG. 1. Specifically, in the default settings of the ultrasound imaging apparatus 3, the first switching unit 304 outputs B-mode image data to the superimposing unit 310 and the storage unit 314 (the image data storage unit 314a), and the second switching unit 305 outputs frequency spectrum data to the storage unit 314 (the spectrum data storage unit 314b).

At Step S1, when the observation of the subject such as a tissue inside the human body is started, the ultrasound transducer 21 scans the subject and converts the echo received from the subject into an electrical echo signal. The transmitting/receiving unit 301 receives the echo signal via the ultrasound endoscope 2. The transmitting/receiving unit 301 amplifies the echo signal. Subsequently, the transmitting/receiving unit 301 samples and discretizes the amplified echo signal at an appropriate sampling frequency (e.g., 50 MHz) to generate RF data and outputs the RF data to the B-mode image data generating unit 302 and the frequency analyzing unit 303.

At Step S2, the B-mode image data generating unit 302 executes amplification (STC correction) on the RF data based on the relationship between the amplification factor and the receiving depth illustrated in FIG. 2, for example. The B-mode image data generating unit 302 generates B-mode image data by using the RF data output from the transmitting/receiving unit 301.

At Step S3, the frequency analyzing unit 303 calculates the frequency spectrum data from the RF data generated at Step S2 (frequency analysis step). The frequency analyzing unit 303 divides the RF data (line data) in each sound ray into multiple portions at a predetermined relatively short time interval and performs FFT operation on the RF data of each of the divided portions to execute frequency analysis so as to calculate the frequency spectrum data on all the RF data strings.

Figure 13:
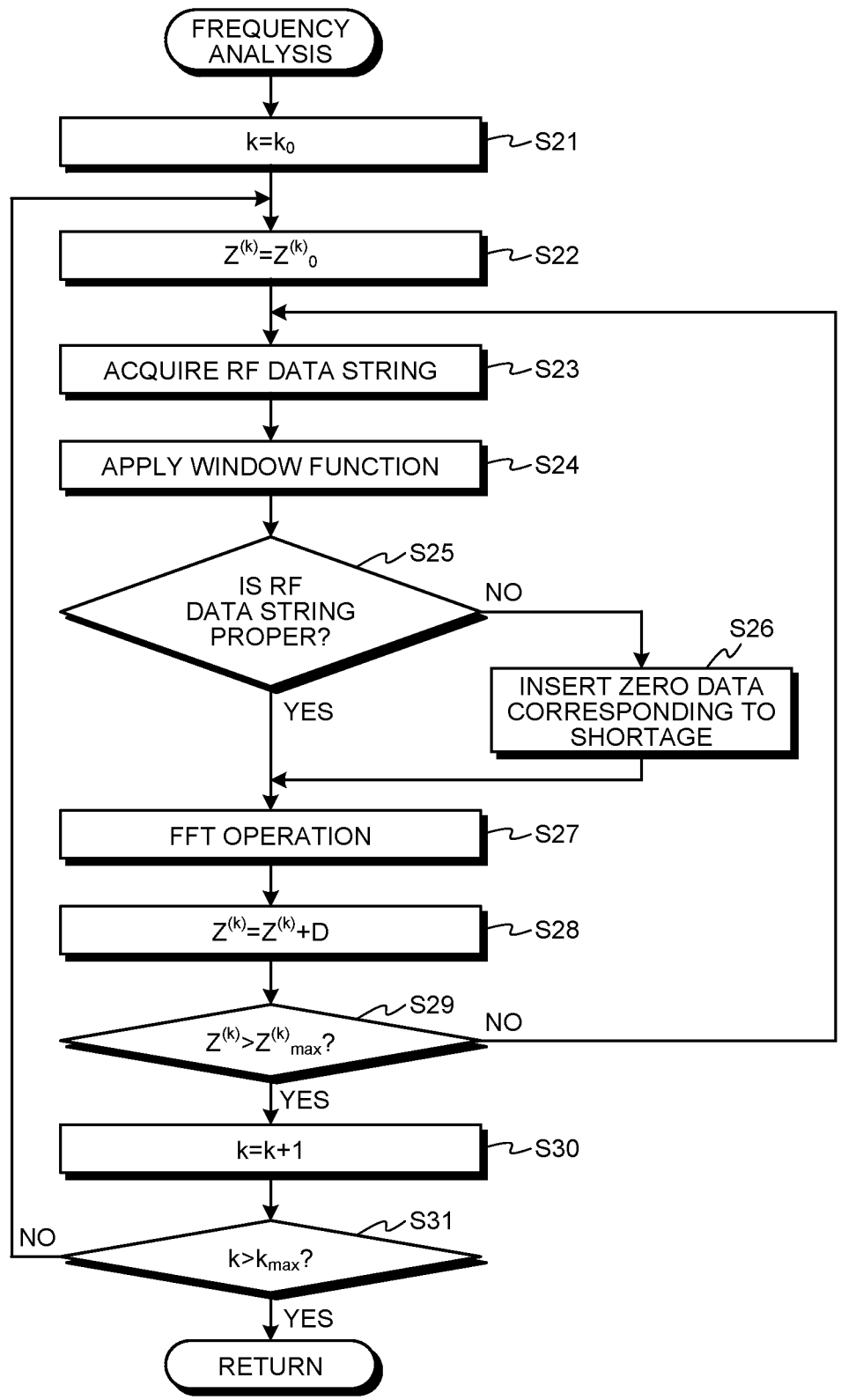
FIG. 13 is a flowchart illustrating the overview of a process performed by the frequency analyzing unit of the ultrasound imaging apparatus according to the first embodiment of the disclosure.

FIG. 13 is a flowchart illustrating the overview of the process performed by the frequency analyzing unit 303 at Step S3. A frequency analysis process is described below in detail with reference to the flowchart illustrated in FIG. 13.

At Step S21, the frequency analyzing unit 303 sets a counter k for identifying the target sound ray to be analyzed as $k_0$. The initial value $k_0$ is the number of the rightmost sound ray in the analysis range in FIG. 3.

At Step S22, the frequency analyzing unit 303 sets the initial value $Z^{(k)}_0$ for a data position (corresponding to the receiving depth) $Z^{(k)}$ representative of the series of RF data strings acquired for the FFT operation. For example, in the case described above in FIG. 4, the eighth data position in the sound ray $SR_k$ is set as the initial value $Z^{(k)}_0$. The initial value $Z^{(k)}_0$ is the data position representative of the shallowest RF data string in the analysis range of the sound ray $SR_k$.

Then, the frequency analyzing unit 303 acquires the RF data string (Step S23) and applies the window function stored in the storage unit 314 to the acquired RF data string (Step S24). Applying the window function to the RF data string as described above makes it possible to avoid the discontinuity of the RF data string at a boundary and to prevent the occurrence of an artifact.

Subsequently, the frequency analyzing unit 303 determines whether the RF data string in the data position $Z^{(k)}$ is a proper RF data string (Step S25). As described with reference to FIG. 4, an RF data string needs to have the number of sets of data that is a power of 2.

Hereinafter, the number of sets of data of a proper RF data string is $2^n$ (n is a positive integer). According to the present embodiment, the data position $Z^{(k)}$ is set to be as much close as possible to the center of the RF data string to which $Z^{(k)}$ belongs. Specifically, as the number of sets of data in the RF data string is $2^n$, $Z^{(k)}$ is set to be at the $2^n/2$ ($=2^{n-1}$)-th position close to the center of the RF data string. In this case, the fact that the RF data string is proper means that there are $2^{n-1}-1$ (=N) sets of data on the side shallower than the data position $Z^{(k)}$ and there are $2^{n-1}$ (=M) sets of data on the side deeper than the data position $Z^{(k)}$. In the case illustrated in FIG. 4, RF data strings $F_1$, $F_2$, $F_3$, ..., and $F_{K-1}$ are all proper. Furthermore, in the case illustrated in FIG. 4, n=4 (N=7, M=8).

When the RF data string at the data position $Z^{(k)}$ is proper as a result of the determination at Step S25 (Step S25: Yes), the frequency analyzing unit 303 proceeds to Step S27 described below.

When the RF data string at the data position $Z^{(k)}$ is not proper as a result of the determination at Step S25 (Step S25: No), the frequency analyzing unit 303 inserts zero data corresponding to a shortage to generate a proper RF data string (Step S26). Before zero data is added, the window function is applied to the RF data string (e.g., the RF data string $F_K$ in FIG. 5) that is determined to be improper at Step S25. Therefore, there is no occurrence of discontinuity in the data even if zero data is inserted into the RF data string. After Step S26, the frequency analyzing unit 303 proceeds to Step S27 described below.

At Step S27, the frequency analyzing unit 303 performs the FFT operation on the RF data string to calculate V(f, L) corresponding to the frequency distribution of the voltage amplitude of the echo signal. Subsequently, the frequency analyzing unit 303 performs logarithmic conversion processing on V(f, L) to obtain the frequency spectrum data S(f, L) (Step S27).

At Step S28, the frequency analyzing unit 303 changes the data position $Z^{(k)}$ by a step range D. It is assumed that, with regard to the step range D, the storage unit 314 previously stores the input value from the operator via the keyboard 5. In the case illustrated in FIG. 4, D=15.

Subsequently, the frequency analyzing unit 303 determines whether the data position $Z^{(k)}$ is larger than a maximum value $Z^{(k)}_{max}$ in the sound ray $SR_k$ (Step S29). The maximum value $Z^{(k)}_{max}$ is a data position representative of the deepest RF data string in the analysis range of the sound ray $SR_k$. When the data position $Z^{(k)}$ is larger than the maximum value $Z^{(k)}_{max}$ (Step S29: Yes), the frequency analyzing unit 303 increments the counter k by one (Step S30). This means that the process proceeds to the subsequent sound ray. Conversely, when the data position $Z^{(k)}$ is equal to or less than the maximum value $Z^{(k)}_{max}$ (Step S29: No), the frequency analyzing unit 303 returns to Step S23.

After Step S30, the frequency analyzing unit 303 determines whether the counter k is larger than a maximum value $k_{max}$ (Step S31). When the counter k is larger than $k_{max}$ (Step S31: Yes), the frequency analyzing unit 303 ends the series of frequency analysis processes. Conversely, when the counter k is equal to or less than $k_{max}$ (Step S31: No), the frequency analyzing unit 303 returns to Step S22. The maximum value $k_{max}$ is the number of the leftmost sound ray in the analysis range in FIG. 3.

As described above, the frequency analyzing unit 303 performs the FFT operation on each of the $(k_{max}-k_0+1)$ sound rays in the analysis target region multiple times for each depth. The storage unit 314 (the spectrum data storage unit 314b) stores a result of the FFT operation together with the receiving depth and the receiving direction.

Furthermore, with regard to the four types of values $k_0$, $k_{max}$, $Z^{(K)}_0$, and $Z^{(k)}_{max}$, the storage unit 314 previously stores the default values such that the entire scan region in FIG. 3 is included, and the frequency analyzing unit 303 reads the values as appropriate to perform the process in FIG. 13. When the default values are read, the frequency analyzing unit 303 performs the frequency analysis processing on the entire scan region. However, the four types of values $k_0$, $k_{max}$, $Z^{(K)}_0$, and $Z^{(k)}_{max}$ may be changed in accordance with the input of the instruction of the region of interest by the operator via the keyboard 5. When a change is made, the frequency analyzing unit 303 performs the frequency analysis processing exclusively on the region of interest for which an instruction has been input.

A description is given with reference back to FIG. 12 again. Step S2 and Step S3 may be performed in a reversed order or may be performed in parallel.

At Step S4, the control unit 313 checks whether the instruction of cauterization with a cautery needle has been input from the operator via a button (not illustrated) or a menu (not illustrated) of the ultrasound endoscope 2 or the keyboard 5. When the cauterization instruction has been input (Step S4: Yes), the control unit 313 proceeds to Step S5. Conversely, when the cauterization instruction has not been input from the keyboard 5 (Step S4: No), the control unit 313 proceeds to Step S13.

At Step S5, the control unit 313 switches the outputs of the first switching unit 304 and the second switching unit 305. Specifically, during the switching process at Step S5, the respective outputs, illustrated in FIG. 1, of the first switching unit 304 and the second switching unit 305 are switched to be in contact with the respective upper right terminals. That is, the transmission path of the first switching unit 304 for giving output to the superimposing unit 310 and the storage unit 314 (the image data storage unit 314a) are switched to the transmission path for giving output to the displacement amount estimating unit 306 and the superimposing unit 310. Furthermore, the transmission path of the second switching unit 305 for giving output to the storage unit 314 (the spectrum data storage unit 314b) is switched to the transmission path for giving output to the differential feature data calculating unit 308 (see FIG. 1).

At Step S6, the B-mode image data generating unit 302 executes amplification (STC correction) on the RF data received by the transmitting/receiving unit 301 after the cauterization instruction is input to generate B-mode image data. The RF data obtained here is during-cauterization RF data.

At Step S7, the frequency analyzing unit 303 calculates frequency spectrum data from the RF data generated at Step S6. In the same manner as that at the above-described Step S3, the frequency analyzing unit 303 divides the RF data (line data) in each sound ray into multiple portions at a predetermined relatively short time interval and performs FFT operation on the RF data of each divided portion to execute frequency analysis so as to calculate frequency spectrum data for all the RF data strings. Furthermore, Step S6 and Step S7 may be performed in a reversed order or may be performed in parallel.

At Step S8, based on the before-cauterization B-mode image and the during-cauterization B-mode image, the displacement amount estimating unit 306 estimates how much the subject or a part thereof (a blood vessel or a tumor) depicted in the before-cauterization B-mode image has been displaced in the during-cauterization B-mode image. Then, the reading unit 307 reads the frequency spectrum data acquired before cauterization from the storage unit 314 (the spectral data storage unit 314b) and executes coordinate conversion with the displacement amount estimated by the displacement amount estimating unit 306. The reading unit 307 outputs the frequency spectrum data having undergone the coordinate conversion to the differential feature data calculating unit 308.

At Step S9, the differential spectrum calculating unit 308a subtracts the before-cauterization frequency spectrum data having undergone coordinate conversion from the during-cauterization frequency spectrum data with the direction and the depth, the Cartesian coordinates defined by the direction and the depth, and the frequency matched to each other. The differential spectrum calculating unit 308a calculates the difference between the sets of frequency spectrum data with regard to each frequency as described above to calculate the differential spectrum data (see FIG. 10).

At Step S10, the regression analysis unit 308b approximates multiple sets of differential spectrum data output from the differential spectrum calculating unit 308a with a straight line to calculate the differential feature data of the differential spectrum data so as to acquire the differential feature data (see FIG. 11). Steps S9 and S10 described above correspond to a differential feature data calculation step.

At Step S11, the analysis image data generating unit 309 generates the analysis image data in which the visual information associated with the differential feature data calculated by the regression analysis unit 308b is assigned to each corresponding pixel of the image in the B-mode image data (an analysis image data generation step).

At Step S12, the superimposing unit 310 synthesizes the B-mode image data generated by the B-mode image data generating unit 302 at Step S6 with the analysis image data generated by the analysis image data generating unit 309 at Step S11 to generate the superimposition image data in which the visual information related to the differential feature data is superimposed on each pixel of the image in the B-mode image data and outputs the superimposition image data to the display image data generating unit 311. After the generated superimposition image data is output to the display image data generating unit 311, the control unit 313 proceeds to Step S14.

Here, at Step S4, when there is no cauterization instruction and only the B-mode image data is input (Step S4: No), the superimposing unit 310 does not superimpose analysis image data but outputs the B-mode image data to the display image data generating unit 311 without change (Step S13). After the B-mode image data is output to the display image data generating unit 311, the control unit 313 proceeds to Step S14.

At Step S14, the display image data generating unit 311 performs, on the superimposition image data generated by the superimposing unit 310 or the B-mode image data, predetermined processing such as gradation processing or data decimation corresponding to the display range of an image on the display device 4 to generate display image data.

Figure 14:
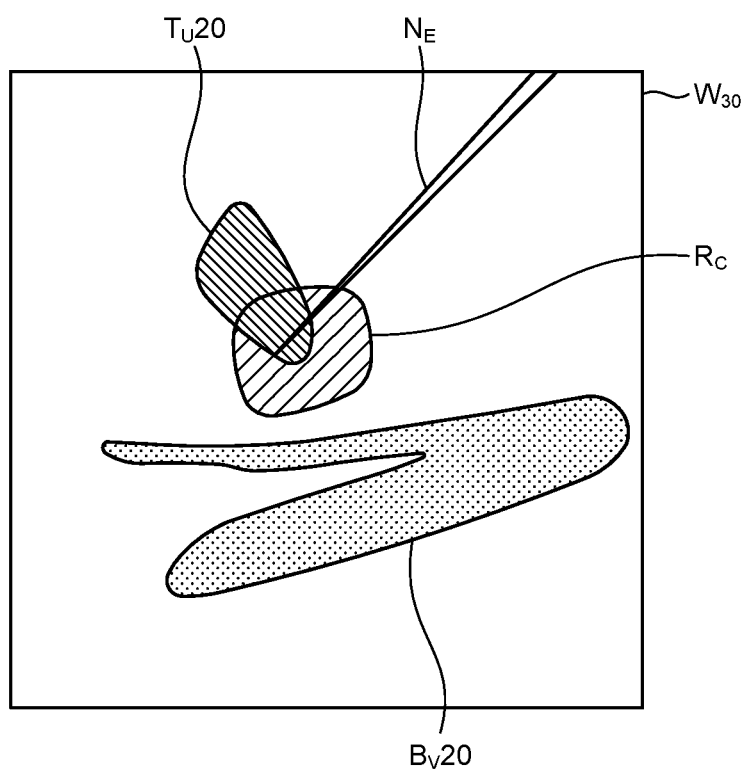
FIG. 14 is a diagram schematically illustrating a display example of a superimposition image in a display device of the ultrasound imaging apparatus according to the first embodiment of the disclosure.

Subsequently, the control unit 313 causes the display device 4 to present the image corresponding to the display image data (Step S15). FIG. 14 illustrates a display example of the image (referred to as superimposition image) corresponding to the superimposition image data. The display screen of the display device 4 displays a superimposition image $W_{30}$ in which a cauterization region $R_c$ generated based on the differential feature data is superimposed on the B-mode image acquired during cauterization. By performing the above-described process, the display device 4 may display the superimposition image representing the cauterization region in real time.

At Step S16, the control unit 313 determines whether the transmitting/receiving unit 301 has received a new echo signal from the ultrasound endoscope 2. When it is determined that the transmitting/receiving unit 301 has received a new echo signal (Step S16: Yes), the control unit 313 proceeds to Step S4 to repeat the above-described process. Conversely, when no new echo signal has been received, for example, when no echo signal has been received even though a predetermined period of time has elapsed after the previous echo signal was acquired (Step S16: No), the control unit 313 ends the process.

Although the first embodiment is described by using the image and the frequency spectrum data before cauterization and various images and various kinds of data during cauterization, after-cauterization images or data may be used instead of during-cauterization images or data as long as the images and the data are acquired after before-cauterization images and data. This point has been described above.

According to the first embodiment of the disclosure described above, differential spectrum data is calculated from the before-cauterization frequency spectrum data and the during-cauterization/after-cauterization frequency spectrum data, calculated by the frequency analyzing unit 303, and differential feature data is calculated from the differential spectrum data. Here, the before-cauterization frequency spectrum data is subjected to coordinate conversion based on the displacement amount of the subject or a part thereof (a blood vessel or a tumor) estimated from the before-cauterization B-mode image data and the during-cauterization/after-cauterization B-mode image data, and the position of the before-cauterization frequency spectrum data is associated with the position of the during-cauterization/after-cauterization frequency spectrum data. As described above, according to the first embodiment of the disclosure, when multiple sets of image information having different time phases are acquired, highly-reproducible image information may be acquired. Thus, according to the first embodiment, the cauterization region, which is the difference information from the before-cauterization B-mode image, may be accurately displayed on the during-cauterization/after-cauterization B-mode image.

Furthermore, according to the first embodiment of the disclosure, echo signals having different time phases are simply acquired to obtain a superimposition image; therefore, when a comparison image before and after treatment is generated, it is possible to suppress an increase in the surgical time and to reduce loads on the patient.

Furthermore, according to the first embodiment of the disclosure, as the differential feature data of the frequency spectra acquired from the identical subject is calculated, it is possible to eliminate the effect of attenuation of an echo signal and to acquire the image data having reproducibility in different time phases and representing an objective difference. In particular, using the differential feature data b (intercept) as differential feature data makes it possible to observe the frequency spectrum at 0 MHz and to acquire the image data from which the effect of attenuation is further eliminated.

Furthermore, according to the first embodiment of the disclosure, echo signals are acquired by using the identical ultrasound probe before cauterization and during/after cauterization to calculate the frequency spectrum; therefore, it is possible to acquire reproducible image data from which the effect of a device difference, such as a difference in the sensitivity of an ultrasound probe, is eliminated.

Moreover, according to the first embodiment of the disclosure, the completion of a treatment may be determined by detecting that the difference in the frequency spectrum data has decreased or that the difference has largely changed once and then has not changed. This detection process allows the operator to understand the completion of the treatment.

Second Embodiment

Figure 15:
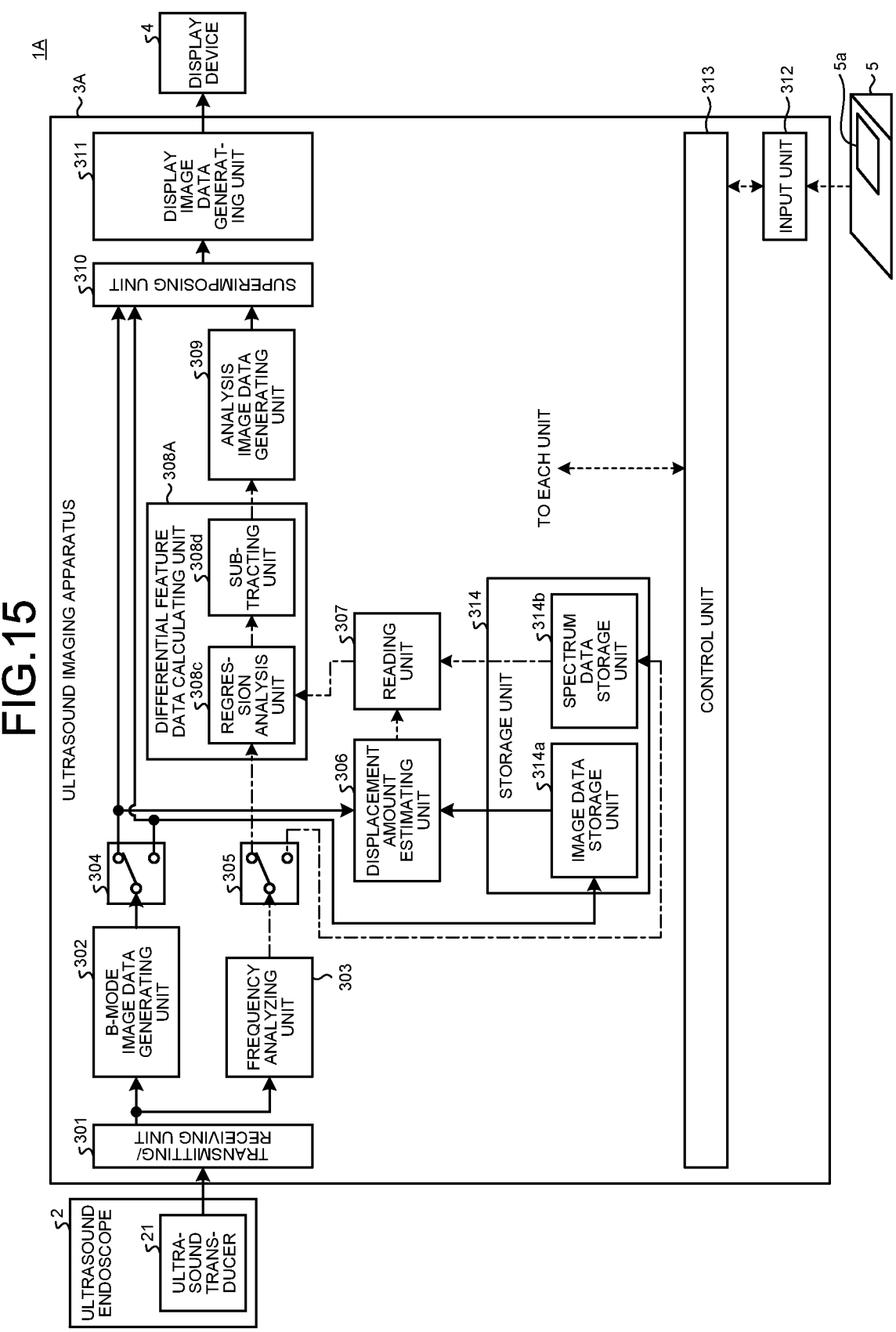
FIG. 15 is a block diagram illustrating a configuration of an ultrasound imaging system including an ultrasound imaging apparatus according to a second embodiment of the disclosure.

Next, a second embodiment of the disclosure is described. FIG. 15 is a block diagram illustrating a configuration of an ultrasound imaging system 1A including an ultrasound imaging apparatus 3A according to the second embodiment of the disclosure. In the above description according to the first embodiment, the differential feature data calculating unit 308 calculates the differential spectrum data so as to calculate the differential feature data from the differential spectrum data; however, according to the second embodiment, a differential feature data calculating unit 308A calculates the respective feature data from the before-cauterization frequency spectrum data and the during-cauterization/after-cauterization frequency spectrum data and uses the before-cauterization feature data and the during-cauterization/after-cauterization feature data to calculate the differential feature data. Moreover, according to the present embodiment, too, after-cauterization images or data may be used instead of during-cauterization images or data as long as the images and the data are acquired after before-cauterization images and data, and therefore during-cauterization and after-cauterization are described as during-cauterization/after-cauterization without being distinguished from each other.

The ultrasound imaging system 1A according to the second embodiment includes the ultrasound imaging apparatus 3A instead of the ultrasound imaging apparatus 3 in the configuration of the ultrasound imaging system 1 according to the above-described first embodiment. The ultrasound imaging apparatus 3A includes a differential feature data calculating unit 308A instead of the differential feature data calculating unit 308 described above. In the ultrasound imaging apparatus 3A, the configuration other than the differential feature data calculating unit 308A is the same as the configuration of the ultrasound imaging apparatus 3 described above.

The differential feature data calculating unit 308A calculates the differential feature data based on the during-cauterization/after-cauterization frequency spectrum data calculated by the frequency analyzing unit 303 and the before-cauterization frequency spectrum data acquired from the reading unit 307. The differential feature data calculating unit 308A includes a regression analysis unit 308c and a subtracting unit 308d.

Specifically, as is the case with the regression analysis unit 308b described above, with regard to the before-cauterization frequency spectrum data and the during-cauterization/after-cauterization frequency spectrum data, the regression analysis unit 308c executes single regression analysis on the frequency spectrum data in a predetermined frequency band to approximate the frequency spectrum data with a linear expression (regression line) so as to calculate the feature data that defines the approximated linear expression. Therefore, the regression analysis unit 308c calculates the before-cauterization feature data and the during-cauterization/after-cauterization feature data.

Figure 16:
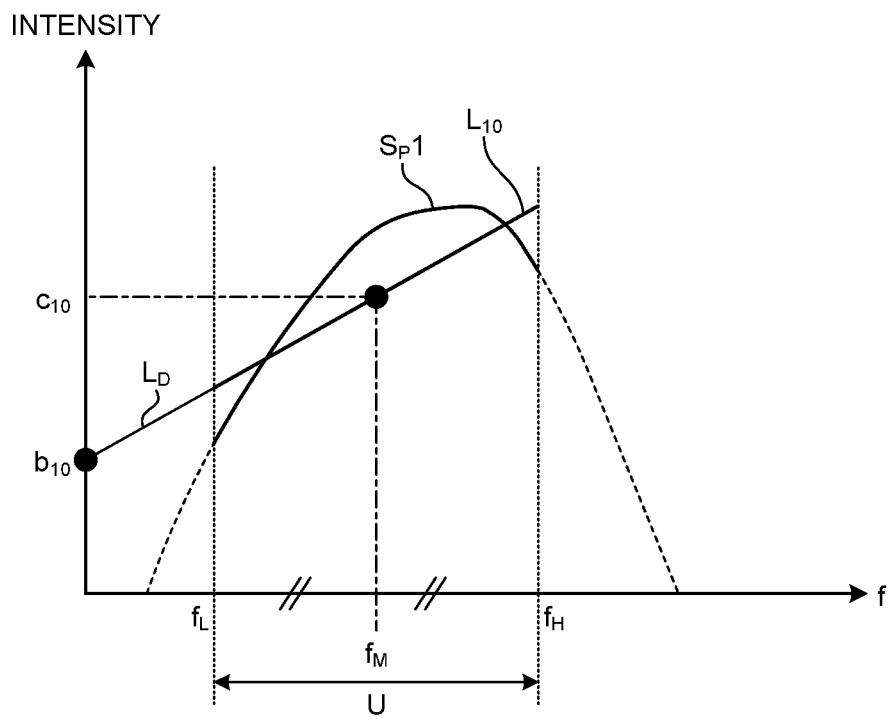
FIG. 16 is a graph illustrating the calculation of frequency feature data using a before-cauterization frequency spectrum.

FIG. 16 is a graph illustrating the calculation of frequency feature data using a before-cauterization frequency spectrum. For example, the regression analysis unit 308c executes single regression analysis on the before-cauterization frequency spectrum data $S_P1$ (see FIG. 9) in the frequency band U to obtain a regression line $L_{10}$ of the before-cauterization frequency spectrum data $S_P1$ (see FIG. 16). Subsequently, the regression analysis unit 308c calculates, as feature data, a slope $a_{10}$, an intercept $b_{10}$, and a mid-band fit $c_{10}=a_{10}f_M+b_{10}$ of the regression line $L_{10}$.

Figure 17:
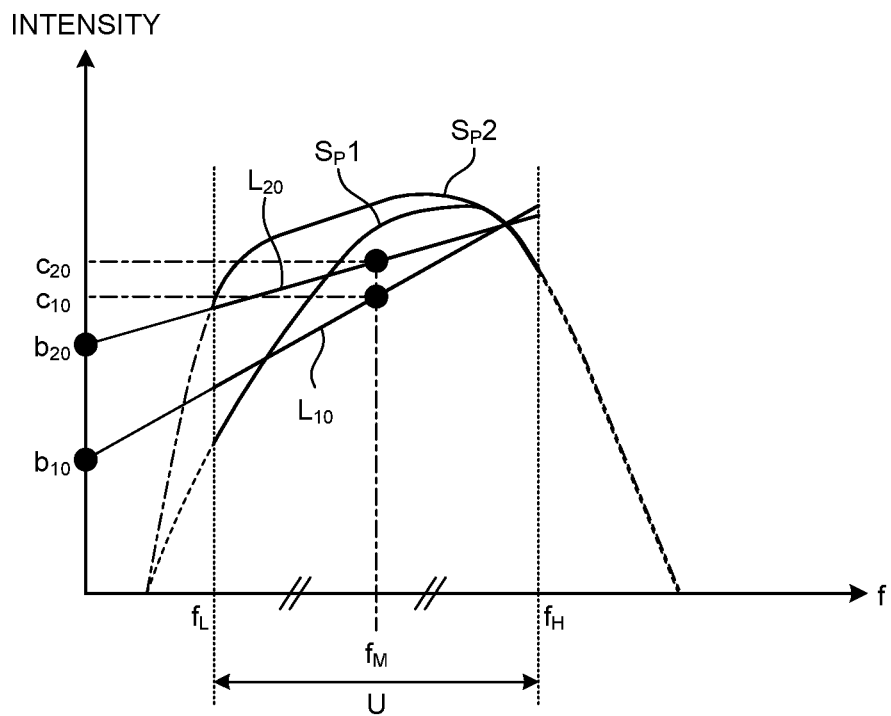
FIG. 17 is a graph illustrating the calculation of differential feature data performed by a differential feature data calculating unit according to the second embodiment of the disclosure.

FIG. 17 is a graph illustrating the calculation of differential feature data performed by the differential feature data calculating unit 308A according to the second embodiment of the disclosure and is a graph illustrating a regression line calculated from the before-cauterization frequency spectrum data and a regression line calculated from the during-cauterization/after-cauterization frequency spectrum data. As illustrated in FIG. 17, the regression analysis unit 308c calculates the feature data $a_{10}$, $b_{10}$, and $c_{10}$ from the regression line $L_{10}$ generated based on the before-cauterization frequency spectrum data $S_P1$ and also calculates feature data $a_{20}$, $b_{20}$, and $c_{20}$ from a regression line $L_{20}$ generated based on the during-cauterization/after-cauterization frequency spectrum data $S_P2$ (see FIG. 9).

The subtracting unit 308d calculates differential feature data that is the difference between the before-cauterization feature data and the during-cauterization/after-cauterization feature data. When the mid-band fit c is used as feature data, for example, the subtracting unit 308d calculates the difference between the feature data $c_{20}$ based on the frequency spectrum data $S_P2$ obtained during cauterization and the feature data $c_{10}$ based on the frequency spectrum data $S_P1$ obtained before cauterization to acquire differential feature data.

The processes to generate and display the superimposition image according to the second embodiment are the same as those in the flowchart illustrated in FIG. 12 except that Steps S9 and S10 are replaced with the above-described process.

According to the second embodiment of the disclosure described above, the respective feature data are calculated from the before-cauterization frequency spectrum data and the during-cauterization/after-cauterization frequency spectrum data, calculated by the frequency analyzing unit 303, and differential feature data is obtained from the feature data. Here, as is the case with the first embodiment, the before-cauterization frequency spectrum data is subjected to coordinate conversion based on the displacement amount of the subject or a part thereof (a blood vessel or a tumor) estimated from the before-cauterization B-mode image data and the during-cauterization/after-cauterization B-mode image data, and the position of the before-cauterization frequency spectrum data is associated with the position of the during-cauterization/after-cauterization frequency spectrum data. Thus, according to the second embodiment of the disclosure, when multiple sets of image information having different time phases are acquired, highly-reproducible image information may be acquired. Thus, according to the second embodiment, the cauterization region, which is the difference information from the before-cauterization B-mode image, may be accurately displayed on the during-cauterization/after-cauterization B-mode image.

Furthermore, according to the second embodiment described above, the regression analysis unit 308c may execute attenuation correction on the feature data calculated from frequency spectrum data. In general, the amplitude of an ultrasound wave attenuates exponentially with respect to a propagation distance. Therefore, when the amplitude is logarithmically transformed to a common logarithm and represented in decibel, the amplitude attenuates linearly with respect to the reciprocation distance L and also attenuates linearly with respect to the receiving depth z (=L/2) that obtains the reciprocation distance L. Therefore, in the decibel representation of the amplitude, an attenuation A(f, z) generated while an ultrasound wave reciprocates between the receiving depth 0 and the receiving depth z may be expressed as a linear change (a difference in the decibel representation) of the amplitude before and after the ultrasound wave reciprocates. It is known that the attenuation A(f, z) of the amplitude depends on a frequency when the subject is a living body; the attenuation is large at a high frequency, and the attenuation is small at a low frequency. In particular, it is empirically known that the attenuation is proportional to the frequency in a uniform tissue and is represented by the following Equation (7).

$$A(f,z) = 2\zeta z f \tag{7}$$

Here, a proportional constant $\zeta$ is a value called an attenuation rate. Furthermore, z is the receiving depth of an ultrasound wave, and f is a frequency. A specific value of the attenuation rate $\zeta$ is determined depending on a site or tissue of a living body when the subject is a living body. In a normal liver, the specific value is approximately 0.55 dB/cm/MHz. Furthermore, the storage unit 314 previously stores the value of the attenuation rate $\zeta$, and the regression analysis unit 308c reads and uses the value of the attenuation rate $\zeta$ from the storage unit 314 as appropriate. When the ultrasound imaging apparatus 3A previously receives the input of a site name or a tissue name of the subject from the operator before the ultrasound endoscope 2 transmits ultrasound waves, the regression analysis unit 308c reads an appropriate value of the attenuation rate $\zeta$ corresponding to the site name or the tissue name and uses the value for the following attenuation correction. Further, when the ultrasound imaging apparatus 3A directly receives the value of the attenuation rate $\zeta$ from the operator, the regression analysis unit 308c uses the value for the following attenuation correction. When the ultrasound imaging apparatus 3A does not receive any input from the operator at all, the regression analysis unit 308c uses 0.55 dB/cm/MHz described above for the following attenuation correction.

The regression analysis unit 308c executes attenuation correction on the calculated feature data (e.g., a slope $a_0$, an intercept $b_0$, and a mid-band fit $c_0$) in accordance with Equations (8) to (10) described below to calculate corrected feature data a, b, and c.

$$a = a_0 + 2\zeta z \tag{8}$$

$$b = b_0 \tag{9}$$

$$c = c_0 + A(f_M, z) = c_0 + 2\zeta z f_M (= af_M + b) \tag{10}$$

As it is understood from Equations (8) and (10), the regression analysis unit 308c executes larger correction on a slope and a mid-band fit as the receiving depth z of the ultrasound wave is larger. Further, according to Equation (9), the correction on an intercept is identical transformation. This is because the intercept is a frequency component corresponding to the frequency of zero (Hz) and is not affected by attenuation.

Subsequently, the regression analysis unit 308c outputs the corrected feature data a, b, and c having undergone the attenuation correction to the subtracting unit 308d. The subtracting unit 308d calculates the difference between the during-cauterization/after-cauterization corrected feature data and the before-cauterization corrected feature data to acquire differential feature data.

Although the embodiments for carrying out the disclosure have been described above, the disclosure should not be limited only to the above-described embodiments. For example, the ultrasound imaging apparatus may be configured such that the circuits having various functions are coupled to each other via a bus or a part of the functions are incorporated in the circuit structure for the other functions.

Although the ultrasound endoscope 2 including an optical system such as a light guide is used as an ultrasound probe in the description according to the first embodiment and the second embodiment, an ultrasound probe including no imaging optical system or imaging element may be used instead of the ultrasound endoscope 2. Further, as an ultrasound probe, an ultrasound miniature probe having a small diameter and including no optical system may be used. The ultrasound miniature probe is usually inserted into a bile tract, bile duct, pancreatic duct, trachea, bronchus, urethra, or urinary duct and is used to observe the surrounding organ (pancreas, lung, prostate, bladder, lymph node, etc.).

Further, an external ultrasound probe that emits ultrasound waves from the body surface of the subject may be used as an ultrasound probe. The external ultrasound probe is typically used in direct contact with the body surface to observe an abdominal organ (liver, gallbladder, or bladder), breast (particularly mammary gland), or thyroid gland.

Further, the ultrasound transducer 21 may be a linear transducer, a radial transducer, or a convex transducer as long as the models are different from each other. The scan region is shaped like a rectangle (a rectangular shape or a square shape) when the ultrasound transducer is a linear transducer, and the scan region is shaped like a fan or a circle when the ultrasound transducer is a radial transducer or a convex transducer. Further, in the ultrasound transducer 21, piezoelectric elements may be arranged in two dimensions. Moreover, the ultrasound endoscope may cause the ultrasound transducer to execute scanning mechanically, include a plurality of elements arranged in an array as an ultrasound transducer to electronically switch the element for transmitting and receiving, or apply a delay to transmission/reception of each element so as to electronically execute scanning.

Furthermore, although the ultrasound probe and the ultrasound imaging apparatus are provided separately in the description, the ultrasound probe and the ultrasound imaging apparatus may be configured to be integrated.

As described above, the disclosure may include various embodiments without departing from the technical idea described in the scope of claims.

INDUSTRIAL APPLICABILITY

As described above, the ultrasound imaging apparatus, the method of operating the ultrasound imaging apparatus, and the computer-readable recording medium according to the disclosure are advantageous in acquiring highly-reproducible image information when multiple sets of image information having different time phases are acquired.

According to the disclosure, it is possible to produce an advantage such that highly-reproducible image information may be acquired when multiple sets of image information having different time phases are acquired.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound imaging apparatus comprising:
   a processor comprising hardware, the processor being configured to:

(a) receive a first ultrasound signal and receive a second ultrasound signal having a different acquisition time from the first ultrasound signal;
(b) generate first ultrasound image data based on the first ultrasound signal and generate second ultrasound image data based on the second ultrasound signal;
(c) generate first frequency spectrum data with regard to the first ultrasound signal and generate second frequency spectrum data with regard to the second ultrasound signal;
(d) estimate a displacement amount including at least one of a positional change amount and a rotation angle of a subject depicted in the first ultrasound image data with respect to the subject depicted in the second ultrasound image data;
(e) correct the first frequency spectrum data in accordance with the estimated displacement amount;
(f) calculate differential feature data by using the corrected first frequency spectrum data and the second frequency spectrum data; and
(g) generate analysis image data to which color information corresponding to the differential feature data is applied.

2. The ultrasound imaging apparatus according to claim 1, wherein the processor is further configured to:
calculate differential spectrum data representing a difference between the corrected first frequency spectrum data and the second frequency spectrum data; and
execute regression analysis on the differential spectrum data to calculate differential feature data.

3. The ultrasound imaging apparatus according to claim 2, wherein the processor is further configured to approximate the corrected first frequency spectrum data and the second frequency spectrum data in a predetermined frequency band with a linear expression to calculate, as the differential feature data, any of an intercept and a slope of the linear expression and a value of the linear expression at an intermediate frequency in the frequency band.

4. The ultrasound imaging apparatus according to claim 1, wherein the processor is further configured to:
execute regression analysis on the corrected first frequency spectrum data to calculate first feature data;
execute regression analysis on the second frequency spectrum data to calculate second feature data; and
perform a subtraction process on the first feature data and the second feature data to calculate differential feature data.

5. The ultrasound imaging apparatus according to claim 1, wherein the processor is further configured to superimpose the analysis image data on the second ultrasound image data.

6. The ultrasound imaging apparatus according to claim 5, wherein the processor is further configured to:
generate the analysis image data in which color information corresponding to corrected differential feature data is assigned to each pixel position of the second ultrasound image data;
superimpose the analysis image data on the second ultrasound image data to generate superimposition image data; and
perform a process corresponding to a display method of a display on the superimposition image data to generate display image data.

7. The ultrasound imaging apparatus according to claim 1, wherein the processor is further configured to:
calculate a correlation value between first converted ultrasound image data obtained by executing coordinate conversion on the first ultrasound image data and the second ultrasound image data; and
estimate the displacement amount based on the correlation value.

8. The ultrasound imaging apparatus according to claim 7, wherein the processor is further configured to:
repeatedly execute the coordinate conversion and the calculation of the correlation value to calculate multiple correlation values; and
estimate the displacement amount based on a case where the largest correlation value is obtained among the multiple correlation values.

9. An ultrasound imaging system comprising:
the ultrasound imaging apparatus according to claim 1; and
an ultrasound probe configured to transmit an ultrasound wave to a subject, receive an ultrasound wave backscattered by the subject, and transmit the received ultrasound wave as an ultrasound signal to the ultrasound imaging apparatus.

10. The ultrasound imaging system according to claim 9, further comprising a display configured to display an image corresponding to the analysis image data.

11. The ultrasound imaging apparatus according to claim 1, wherein the processor is further configured to execute coordinate conversion to the first frequency spectrum data in accordance with the estimated displacement amount to correct the first frequency spectrum data.

12. The ultrasound imaging apparatus according to claim 1, wherein the processor is configured to:
check whether an instruction of cauterization with a cautery needle has been input; and
repeat (a)-(g) during the input.

13. A method of operating an ultrasound imaging apparatus, the method comprising:
receiving a first ultrasound signal and receiving a second ultrasound signal having a different acquisition time from the first ultrasound signal;
generating first ultrasound image data based on the first ultrasound signal and generating second ultrasound image data based on the second ultrasound signal;
generating first frequency spectrum data with regard to the first ultrasound signal and generating second frequency spectrum data with regard to the second ultrasound signal;
estimating a displacement amount including at least one of a positional change amount and a rotation angle of a subject depicted in the first ultrasound image data with respect to the subject depicted in the second ultrasound image data;
correcting the first frequency spectrum data in accordance with the estimated displacement amount;
calculating differential feature data by using the corrected first frequency spectrum data and the second frequency spectrum data; and
generating analysis image data to which color information corresponding to the differential feature data is applied.

14. A non-transitory computer-readable recording medium having an executable program recorded therein, the program instructing a processor to execute:
receiving a first ultrasound signal and receiving a second ultrasound signal having a different acquisition time from the first ultrasound signal;
generating first ultrasound image data based on the first ultrasound signal and generating second ultrasound image data based on the second ultrasound signal;

generating first frequency spectrum data with regard to the first ultrasound signal and generating second frequency spectrum data with regard to the second ultrasound signal;
estimating a displacement amount including at least one of a positional change amount and a rotation angle of a subject depicted in the first ultrasound image data with respect to the subject depicted in the second ultrasound image data;
correcting the first frequency spectrum data in accordance with the estimated displacement amount;
calculating differential feature data by using the corrected first frequency spectrum data and the second frequency spectrum data; and
generating analysis image data to which color information corresponding to the differential feature data is applied.

* * * * *